United States Patent
Askem et al.

(10) Patent No.: US 10,828,403 B2
(45) Date of Patent: Nov. 10, 2020

(54) NEGATIVE PRESSURE WOUND THERAPY APPARATUS AND METHODS FOR OPERATING THE APPARATUS

(71) Applicant: Smith & Nephew PLC, Watford (GB)

(72) Inventors: Ben Alan Askem, East Yorkshire (GB); Allan Kenneth Frazer Grugeon Hunt, Beverley (GB)

(73) Assignee: Smith & Nephew PLC, Watford (GB)

( * ) Notice: Subject to any disclaimer, the term of this patent is extended or adjusted under 35 U.S.C. 154(b) by 577 days.

(21) Appl. No.: 15/540,229

(22) PCT Filed: Dec. 21, 2015

(86) PCT No.: PCT/EP2015/080740
§ 371 (c)(1),
(2) Date: Jun. 27, 2017

(87) PCT Pub. No.: WO2016/107775
PCT Pub. Date: Jul. 7, 2016

(65) Prior Publication Data
US 2018/0200414 A1    Jul. 19, 2018

Related U.S. Application Data

(60) Provisional application No. 62/172,704, filed on Jun. 8, 2015, provisional application No. 62/097,273, filed on Dec. 29, 2014.

(51) Int. Cl.
*A61M 1/00* (2006.01)
*A61F 13/02* (2006.01)
*A61F 13/00* (2006.01)

(52) U.S. Cl.
CPC ......... *A61M 1/009* (2014.02); *A61F 13/0216* (2013.01); *A61M 1/0025* (2014.02);
(Continued)

(58) Field of Classification Search
CPC .. A61M 1/0025; A61M 1/0088; A61M 1/009; A61M 1/0092; A61M 2205/3592;
(Continued)

(56) References Cited

U.S. PATENT DOCUMENTS

| 8,579,872 B2 | 11/2013 | Coulthard et al. |
| 9,265,867 B2 | 2/2016 | Coulthard et al. |

(Continued)

FOREIGN PATENT DOCUMENTS

| WO | WO 2012/057881 | 5/2012 |
| WO | WO 2013/064852 | 5/2013 |

(Continued)

OTHER PUBLICATIONS

International Search Report and Written Opinion, re PCT Appication No. PCT/EP2015/080740, dated Jul. 12, 2016, in 22 pages.

(Continued)

*Primary Examiner* — Benjamin J Klein
(74) *Attorney, Agent, or Firm* — Knobbe, Martens, Olson & Bear, LLP

(57) ABSTRACT

Disclosed embodiments relate to apparatuses and methods for wound treatment. In certain embodiments, a negative pressure wound therapy apparatus includes one or more indicators configured to illuminate in a pattern to communicate at least one of a status of a pump assembly and/or of a dressing. The pattern is configured to enable an electronic device comprising at least one camera to capture the illumination pattern of the one or more indicators and to determine the status corresponding to the pattern of illumination. In some embodiments, a negative pressure wound therapy apparatus is powered by an energy generator that has a first side configured to be in contact with a skin surface of a patient and a second side configured to be exposed to atmosphere, and the energy generator is configured to utilize (Continued)

a temperature differential between the skin surface and the atmosphere to generate electrical energy to power the apparatus. In some embodiments, a negative pressure wound therapy apparatus is powered by an energy harvester that utilizes radio frequency spectrum to power one or more components of negative pressure wound therapy apparatus. In certain embodiments, a negative pressure wound therapy apparatus includes one or more RF energy harvesters to power a pump assembly.

9 Claims, 16 Drawing Sheets

(52) U.S. Cl.
CPC ........ *A61M 1/0088* (2013.01); *A61M 1/0092* (2014.02); *A61F 13/00068* (2013.01); *A61M 2205/3592* (2013.01); *A61M 2205/3673* (2013.01); *A61M 2205/583* (2013.01); *A61M 2205/584* (2013.01); *A61M 2205/6081* (2013.01); *A61M 2205/8237* (2013.01); *A61M 2209/088* (2013.01)

(58) Field of Classification Search
CPC .... A61M 2205/3673; A61M 2205/583; A61M 2205/584; A61M 2205/6081; A61M 2205/8237; A61M 2209/088; A61F 13/00068
See application file for complete search history.

(56) References Cited

U.S. PATENT DOCUMENTS

| | | |
|---|---|---|
| 2006/0281435 A1 | 12/2006 | Shearer et al. |
| 2012/0016322 A1 | 1/2012 | Coulthard et al. |
| 2012/0035562 A1 | 2/2012 | Locke et al. |
| 2013/0110058 A1* | 5/2013 | Adie .................. A61M 1/0031 604/319 |
| 2013/0144227 A1 | 6/2013 | Locke et al. |
| 2014/0005618 A1 | 1/2014 | Locke et al. |
| 2014/0236109 A1 | 8/2014 | Greener |
| 2014/0298928 A1 | 10/2014 | Duesterhoft et al. |
| 2016/0151207 A1 | 6/2016 | Pratt et al. |

FOREIGN PATENT DOCUMENTS

| | | |
|---|---|---|
| WO | WO 2015/050654 | 4/2015 |
| WO | WO 2016/018448 | 2/2016 |
| WO | WO 2016/107775 | 7/2016 |

OTHER PUBLICATIONS

International Preliminary Report on Patentability, re PCT Application No. PCT/EP2015/080740, dated Jul. 13, 2017.
"Ultra high frequency", Wikipedia, accessed Apr. 14, 2020, in 8 pages. URL: https://en.wikipedia.org/wiki/Ultra_high_frequency.
Vyas, R. et al., "Near-perpetual operated solar and RF powered autonomous sensing systems", 2009 Asia Pacific Microwave Conference, IEEE, Dec. 7-10, 2009, pp. 2240-2243, in 4 pages.

* cited by examiner

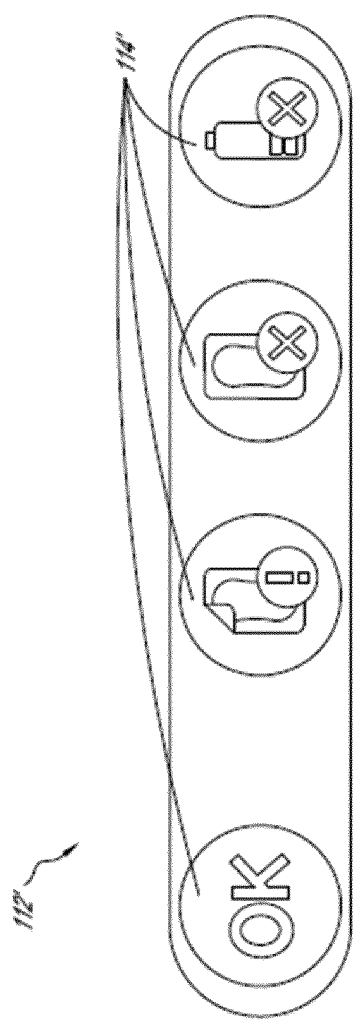

NEGATIVE PRESSURE WOUND THERAPY APPARATUS AND METHODS FOR OPERATING THE APPARATUS

CROSS-REFERENCE TO RELATED APPLICATIONS

This application is a U.S. national stage application of International Patent Application No. PCT/EP2015/080740, filed on Dec. 21, 2015, which claims the benefit of U.S. Provisional Application No. 62/097,273, filed Dec. 29, 2014, and U.S. Provisional Application No. 62/172,704, filed Jun. 8, 2015, the entireties of which are hereby incorporated by reference.

BACKGROUND

Field

Embodiments or arrangements disclosed herein relate to methods and apparatuses for dressing and treating a wound with topical negative pressure therapy. For example but without limitation, any embodiments disclosed herein relate to treating a wound with reduced pressure provided from a pump kit. As another non-limiting example, any embodiments disclosed herein relate to apparatuses and methods for controlling and monitoring the operation of a TNP system.

Background

Many different types of wound dressings are known for aiding in the healing process of a human or animal. These different types of wound dressings include many different types of materials and layers, for example, pads such as gauze pads and/or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing.

SUMMARY

Embodiments of the present disclosure relate to apparatuses and methods for wound treatment. Some of the wound treatment apparatuses described herein comprise a pump system for providing negative pressure to a wound. Wound treatment apparatuses may also comprise wound dressings that may be used in combination with the pump assemblies described herein, and connectors for connecting the wound dressings to the pump assemblies.

In some aspects, an apparatus for use in negative pressure wound therapy, includes a dressing configured to be placed over a wound; a pump assembly, that includes a source of negative pressure, and one or more indicators; and a power source that includes an energy generator (or energy harvester) in electrical communication with the pump assembly. The energy generator has a first side configured to be in contact with a skin surface of a patient and a second side configured to be exposed to atmosphere, and the energy harvester is configured to utilize a temperature differential between the skin surface and the atmosphere to generate electrical energy.

The apparatus of the preceding paragraph may also include any combination of the following features described in this paragraph, among others described herein. The power source may provide power to operate the pump assembly. The power source may provide power to operate components of the dressing, the components including at least one of sensors, Bluetooth, and/or Wi-Fi communication. The energy harvester can include a Quantum well energy harvester. The energy harvester can be embedded within, incorporate into, or positioned on the dressing. The size of the energy harvester can be approximately 1 $cm^2$ to 6 $cm^2$ The power source can generate approximately 5-200 mW. To utilize a power source generating power on the lower end of the range, a capacitor system could be used to temporarily store energy for a minute or two in order to allow continuous running of a drum pump. The power source and the source of negative pressure can be positioned within the dressing. The power source can include multiple energy generators. The dressing assembly, pump assembly, and power source can be configured to be worn by the patient.

In some embodiments, an apparatus for use in negative pressure wound therapy includes a pump assembly, that includes a source of negative pressure, a port configured to be in communication with a dressing assembly, and one or more indicators configured to illuminate in a pattern to communicate at least one of a status of the pump assembly and/or of the dressing. The pattern is configured to enable an electronic device including at least one camera to capture the illumination pattern of the one or more indicators and to determine the status corresponding to the pattern of illumination of the one or more indicators.

The apparatus of the preceding paragraph may also include any combination of the following features described in this paragraph, among others described herein. The one or more indicators can include different color LEDs. The one or more indicators can be configured to flash between the different colors. The different colors can include red and green. The electronic device can include a smartphone or a tablet. The one or more indicators can include four indicators. The one or more indicators can transmit four bits of data at a time to the electronic device. The one or more indicators can be configured to transmit information at a rate of approximately 40 bit/second to 1 Kbit/second.

In certain aspects, a method of operating an apparatus for use in negative pressure wound therapy, includes providing negative pressure wound therapy from a pump assembly fludicially connected to a dressing positioned over a wound, and communicating status of at least one of the pump assembly and the dressing through an illumination pattern of one or more indicators positioned on an exterior surface of the pump assembly. The method also recites communicating the status to an electronic device having at least one camera to capture the illumination of the one or more indicators with the at least one camera and determine the associated status corresponding to the pattern of illumination of the one or more indicators.

In certain aspects, a negative pressure wound therapy apparatus includes a pump assembly which includes a source of negative pressure configured to be fluidically connected to the dressing configured to be placed over a wound and a power source including an energy harvester in electrical communication with the pump assembly. The energy harvester can be configured to receive radio frequency (RF) signals and to generate power from at least some of the received RF signals.

The apparatus of the preceding paragraph may also include any combination of the following features described in this paragraph, among others described herein. The power source can provide power to operate the pump assembly. The pump assembly and the power source can be at least partially embedded into the dressing. The power source can provide power to operate one or more components of the dressing, the one or more components of the dressing can include at least one of sensors or communication devices. The energy harvester can be embedded within, incorporated into, or positioned on the dressing. The RF signals can include intentionally broadcasted RF signals. The RF signals can include environmental RF signals. The power source and the source of negative pressure can be positioned within the dressing. The dressing, pump assembly, and power source can be configured to be worn by the patient.

In some embodiments, a method of operating a negative pressure wound therapy apparatus includes providing negative pressure wound therapy from a pump assembly fluidically connected to a dressing positioned over a wound and operating the pump assembly with a power source including an energy harvester in electrical communication with the pump assembly, wherein the energy harvester is configured to receive radio frequency (RF) signals and to generate power using at least some of the received RF signals.

The method of the preceding paragraph may also include any combination of the following features described in this paragraph, among others described herein. The power source can provide power to operate the pump assembly. The method can also include operating components of the dressing with the power source, the components of the dressing including at least one of sensors or communication devices. The energy harvester can be embedded within, incorporated into, or positioned on the dressing. The RF signals can include intentionally broadcasted RF signals. The RF signals can include environmental RF signals. The power source and the source of negative pressure can be positioned within the dressing. The dressing assembly, pump assembly, and power source can be configured to be worn by the patient.

Any of the features, components, or details of any of the arrangements or embodiments disclosed in this application, including without limitation any of the pump embodiments (for example, any of the voice coil pump embodiments) and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIG. 3 is an embodiment of an arrangement of indicators.

DETAILED DESCRIPTION

Figure 1:
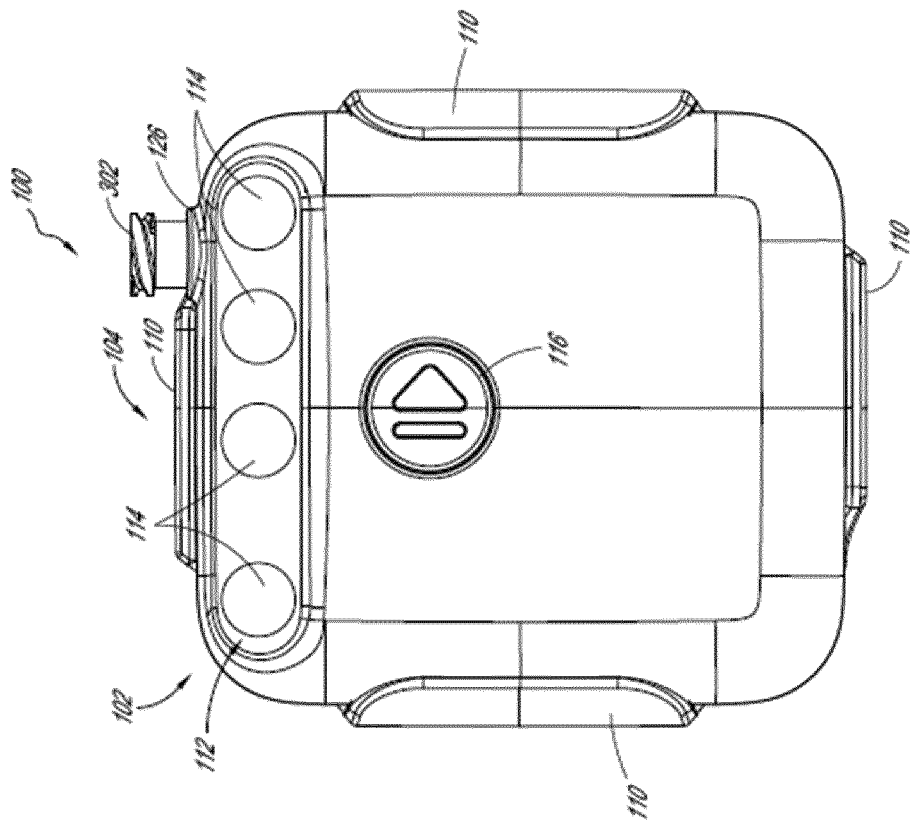
FIG. 1 is a front perspective view of an embodiment of a pump system having an outer housing with a mounting component attached thereto.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments disclosed herein, the components of the TNP system described herein can be particularly suited for incisional wounds that exude a small amount of wound exudate.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

The operating negative pressure range for some embodiments of the present disclosure can be between approximately −20 mmHg and approximately −200 mmHg, between approximately −50 mmHg and approximately −150 mmHg, between approximately −70 mmHg and −90 mmHg, any subrange within these ranges, or any other range as desired. In some embodiments, an operating negative pressure range of up to −70 mmHg, up to −80 mmHg, up to −90 mmHg, up to −100 mmHg, up to −110 mmHg, or up to any other pressure as desired can be used. Other details regarding the operation of the pump system are set forth in U.S. Publication Nos. 2011/0282309, 2013/0110058 and 2013/0331823 as well as International Patent Publication No. WO 2013/171585, and all embodiments, configurations, details, and illustrations of these publications are hereby incorporated by reference in their entireties as if made part of this disclosure.

Any of the embodiments disclosed herein can include a pump and/or a pump and dressing kit. However, the pump apparatuses and embodiments of the present disclosure are not limited to use with a dressing or for wound therapy. Any of the pump embodiments disclosed herein can be used independently of the dressing components disclosed herein. Further, any of the pump embodiments disclosed herein can be used, or can be adapted for use, for other purposes outside of negative pressure wound therapy. As such, any of the pump embodiments disclosed herein can be used, or can be adapted for use, to move fluids (gaseous and/or liquid) in any system or application.

The pump system embodiments described herein can have a compact, small size. In some embodiments disclosed herein, a pump assembly of the pump system can have a diameter (e.g., equivalent diameter) or lateral size in the range of approximately 26 mm to approximately 27 mm, or between approximately 22 mm or smaller and approximately 28 mm In some embodiments disclosed herein, the pump assembly can have a thickness or height of approximately 8 mm, or from approximately 6 and approximately 10 mm. For example and without limitation, in some embodiments the pump assembly can have a volume of approximately 6.26 cubic centimeters, or from approximately 5.0 cubic centimeters or less to approximately 7.0 cubic centimeters. In some embodiments, the housing of the pump can have a lateral size of approximately 60.0 mm, or from between approximately 40.0 mm and approximately 80.0 mm, and a height of approximately 15.0 mm, or from between approximately 10.0 mm and approximately 20.0 mm. The pump system can be any miniaturized size that is manufacturable, and the overall power output and efficiency meet the needed requirements for the desired application, within or outside of wound therapy. As used herein, efficiency can be defined as (fluid power out)/(electrical power in).

The pump system can be produced for a low cost and can operate at high efficiencies, making it beneficial for portable, disposable, and/or single use applications. This pump can optionally be used in an ultra-portable single-use negative-pressure wound therapy (NPWT) device. In some embodiments, the pump system can run for 10 days on a small primary cell without the need for battery replacement or recharging. In some embodiments the pump system can run up to 10 days on a 3V cell of approximately 2000 mAh (e.g., with the pump is working for about 20% of the time). In some embodiments, the pump system can be powered by two 1.5 volt, 2500-3000 mAh batteries connected in parallel. In some embodiments, the pump system can run for a week on a small primary cell such as one or more batteries having a total capacity of 3000 mAh at 3V, which corresponds to 9 Wh or 32.4 kJ (2×1.5V 3000 mAh cells in parallel make 3V, 3000 mAh), without the need for battery replacement or recharging. In some embodiments, the disclosed pump embodiments can be used with a canister or without a canister for collecting exudate or fluids from the wound.

Negative Pressure Wound Therapy System

Figure 2:
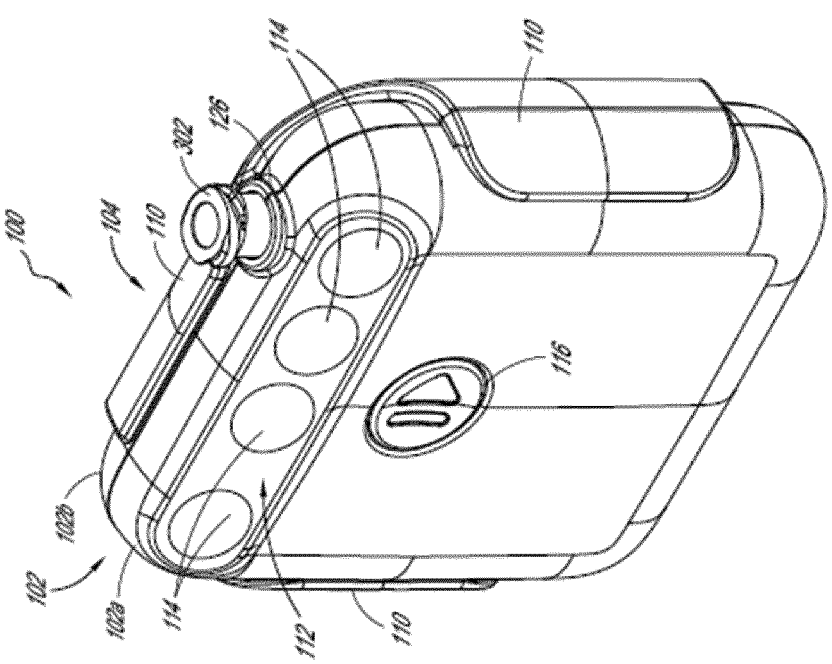
FIG. 2 is a front view of the pump system of FIG. 1.

FIGS. 1-2 illustrate multiple views of an embodiment of a pump system 100 having an outer housing 102 and a mounting component 104. As shown in the illustrated embodiment, the pump system 100 can include an outer housing 102 for containing and/or supporting components of the pump system 100. The outer housing 102 can be formed from one or more portions, such as a front portion 102a and a rear portion 102b as shown in FIG. 1, which can be removably attached to form the outer housing 102.

In some embodiments, the pump system 100 can include a mounting component 104 which can be designed to advantageously allow the pump system 100 to be mounted on another object such as, but not limited to, a user's person. For example, as shown in the illustrated embodiment, the mounting component 104 can include a clip (not shown) designed to retain the mounting component 104 on a user's outerwear, such as on a user's pocket, a pouch, a belt, a flap, or otherwise. The clip can be integrally formed with the base 108 of the mounting component 104 such that the clip can provide a clamping force via resiliency of the material used to form the clip. In some embodiments, the clip can be a separate component from the base 108 and can include a biasing component, such as a coil spring, bent spring or the like, to provide a clamping force to retain the clip on the user's person. In some embodiments, the clamping force can be low enough that a user can open the housing from the clamped position, but strong enough so that it will remain clamped about the pocket, flap, or other material.

In some embodiments, the mounting component 104 can be removably attached to the outer housing 102 such that the pump system 100 can be used with or without the mounting component 104. This can beneficially reduce the overall form factor of the pump system 100 should the user decide to forego use of the mounting component 104. Moreover, this can advantageously allow a user to more easily replace one mounting component with another mounting component should the user decide to do so. As shown in the illustrated embodiment, the mounting component 104 can include one or more retention features. In some embodiments, the retention features can be mechanical fasteners such as screws, nuts, bolts, snap-fit connectors, or the like.

With continued reference to the pump system 100 of FIGS. 1-2, the outer housing 102 can include an interface 112 which can be designed to provide a user with information (e.g., information regarding an operational status of the pump system 100). In some embodiments, the interface 112 can include one or more indicators, such as icons 114, which can alert the user to one or more operating and/or failure conditions of the pump system 100. For example, the indicators can include icons for alerting the user to normal or proper operating conditions, pump failure, power failure, the condition or voltage level of the batteries, the condition or capacity of a wound dressing and/or a canister, detection of a leak within the dressing or fluid flow pathway between the dressing and the pump assembly, suction blockage, or any other similar or suitable conditions or combinations thereof. An exemplary set of icons 114' of an interface 112' is illustrated in FIG. 3 which, from left to right, can include an "OK" indicator which can indicate normal operation of the pump system 100, a "leak" indicator which can indicate the existence of a leak in the pump system 100 or components attached thereto, a "dressing full" indicator which can indicate that a wound dressing is at or near capacity, and a "battery critical" indicator which can indicate that the battery is at or near a critical level. Further, the indicator can be a color or light indicator with or without indicator symbols to indicate a condition or provide information to the user. For example, the lights or illumination components can illuminate one at a time, at the same time, or in certain patterns to indicate a condition or provide information to the user or to the system.

In the illustrated embodiment, one or more indicators 114 can be printed directly on the interface 112 of the outer housing 102. In some embodiments, one or more of the indicators 114 can be provided on a label attached to a portion of the outer housing 102. One or more of the indicators 114 can be illuminated (or active) when the status corresponding to that indicator exists in the system. As will be discussed in further detail below, one or more illumination components, such as LEDs, can be positioned within the outer housing 102 to illuminate the indicators 114. To enhance illumination of the indicators using an illumination component within the outer housing 102, portions of the outer housing 102 proximate and/or underlying one or more of the indicators 114 can be reduced in thickness to increase the translucency of the outer housing 102 proximate and/or underlying the indicators 114. In some embodiments, portions of the outer housing 102 proximate and/or underlying one or more of the indicators 114 can be made from a transparent material. Advantageously, as no openings are formed in the outer housing 102 to provide illumination for the one or more indicators 114, the potential for leakage around the indicators 114 is eliminated or at least significantly reduced.

Communication of Information

In some embodiments, as illustrated in FIGS. 4A-F, the indicators 414 can communicate with an electronic device 416 to provide the user with a status and/or other information relating to the pump system. The indicators 414 can be similar to the indicators 114 described with reference to FIGS. 1-3. The pump system also comprises a port 418 that allows communication with the dressing assembly (not shown). The indicators can also illuminate to communicate the status and/or other information relating to the dressing assembly. However, as illustrated in FIGS. 4A-F, the status or conditions and/or information can be communicated on the interface 412 through a pattern or sequence of illumination of the indicators 414. The state can be communicated by flashing a combination of one or more LEDs.

The illumination of the indicators can be detected by a remote device and the light or illumination pattern can transmit the data to the remote device associated with a certain condition or information relating to the pump system or dressing assembly. This communication with a remote device can be a wireless communication between the light source and a remote optical detector such as a camera. Additionally, in some embodiments, the indicators can be audible, tactile, etc. and thereby can communicate the status and/or information through audible sounds, by touch, etc. In certain embodiments, more than one type of indicator can be used, such as visual, audible, tactile, etc. In some embodiments, the conditions or information communicated by the indicators and read by a remote device can include a transfer of large amount of data from the pump and/or a data log of broader statistics of the operation of the pump. For example, in some embodiments, the illumination of the indicators read by the remote device can communicate the status of the pump and operation of the pump over a period of use or non-use of the pump. The conditions or information communicated can include information relating to the run time of the pump, logs (such as negative pressure levels, time duration during which therapy has been provided, and the like), error conditions (such as interruption of operation), operating negative pressure range, status of power source, dressing status, and the like.

The conditions or information relating to the dressing or pump systems can be communicated or transferred to a computer or electronic device 416. The electronic device 416 can interpret or read the illumination of the indicators 414 or combination of indicators 414 to provide the user with information regarding the dressing system. As shown in FIGS. 4A-F, the interface 412 can include one or more indicators 414 that can be illuminated or activated when a status corresponding to that indicator 414 exists in the system. The indicators 414 can be illuminated one at a time, at the same time, or in a pattern. The illumination or pattern in which the indicators 414 illuminate can be read by an electronic device 416 such as a smartphone, tablet, laptop, or any other suitable portable or stationary electronic device. The pattern displayed by the indicators 414 can be read by the electronic device 416 and can transfer the information relating to the condition of the dressing or pump system to the user or to a computer to be stored for later use.

Figure 4A:
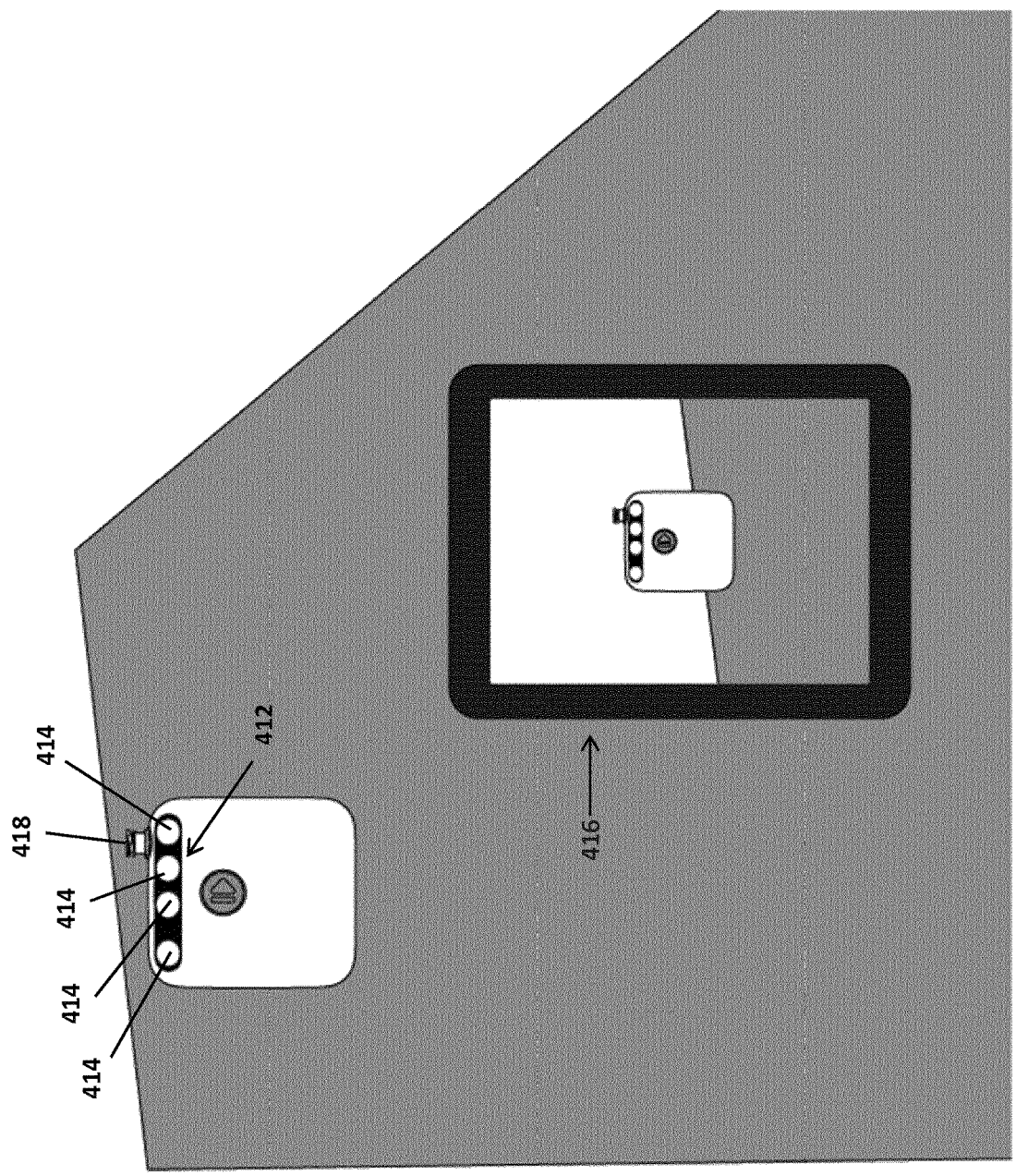
FIGS. 4A-F illustrates one or more indicators that communicate a status corresponding to a pump system and transfer of the status information to an electronic device.
Figure 4B:
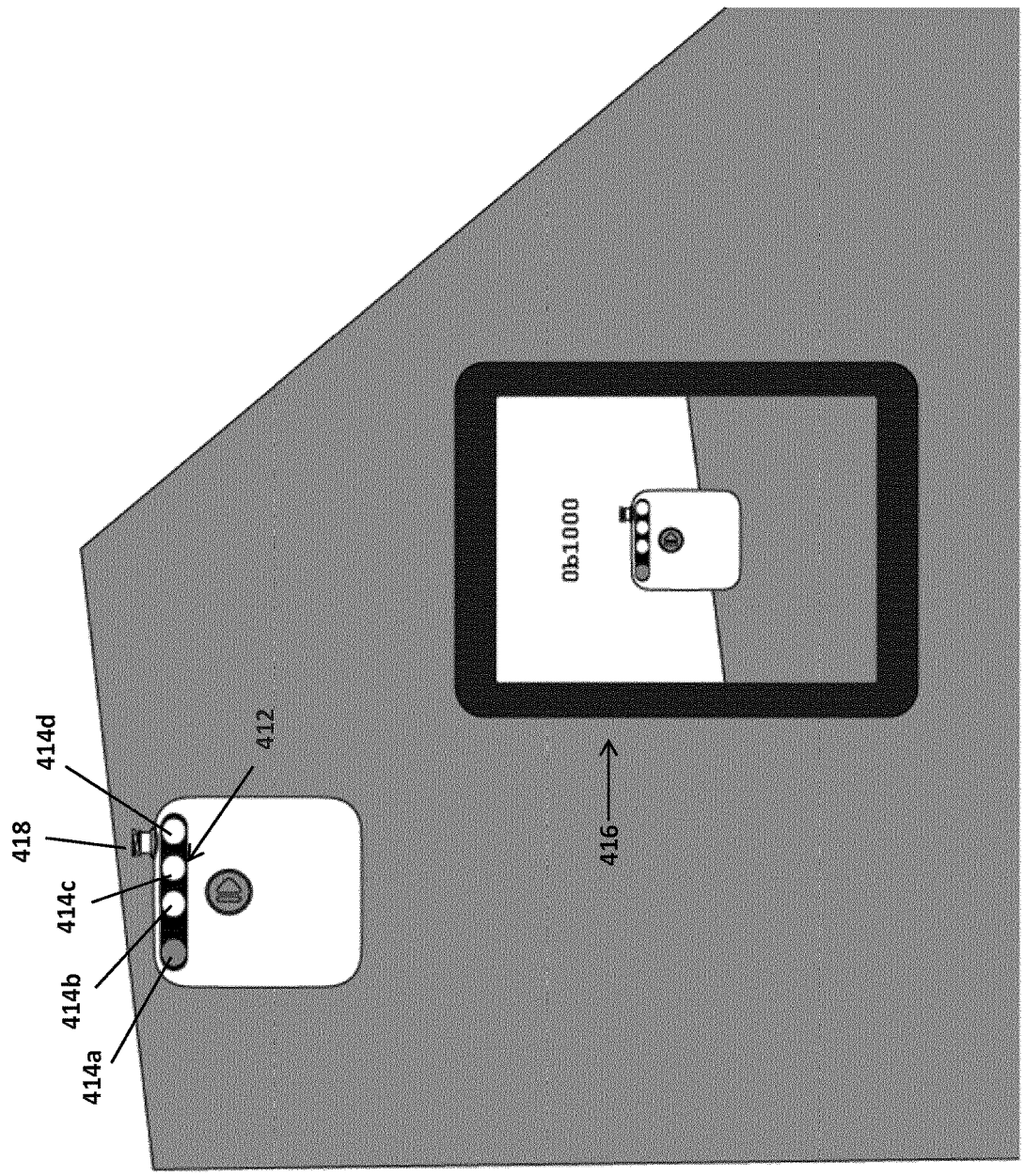
Figure 4C:
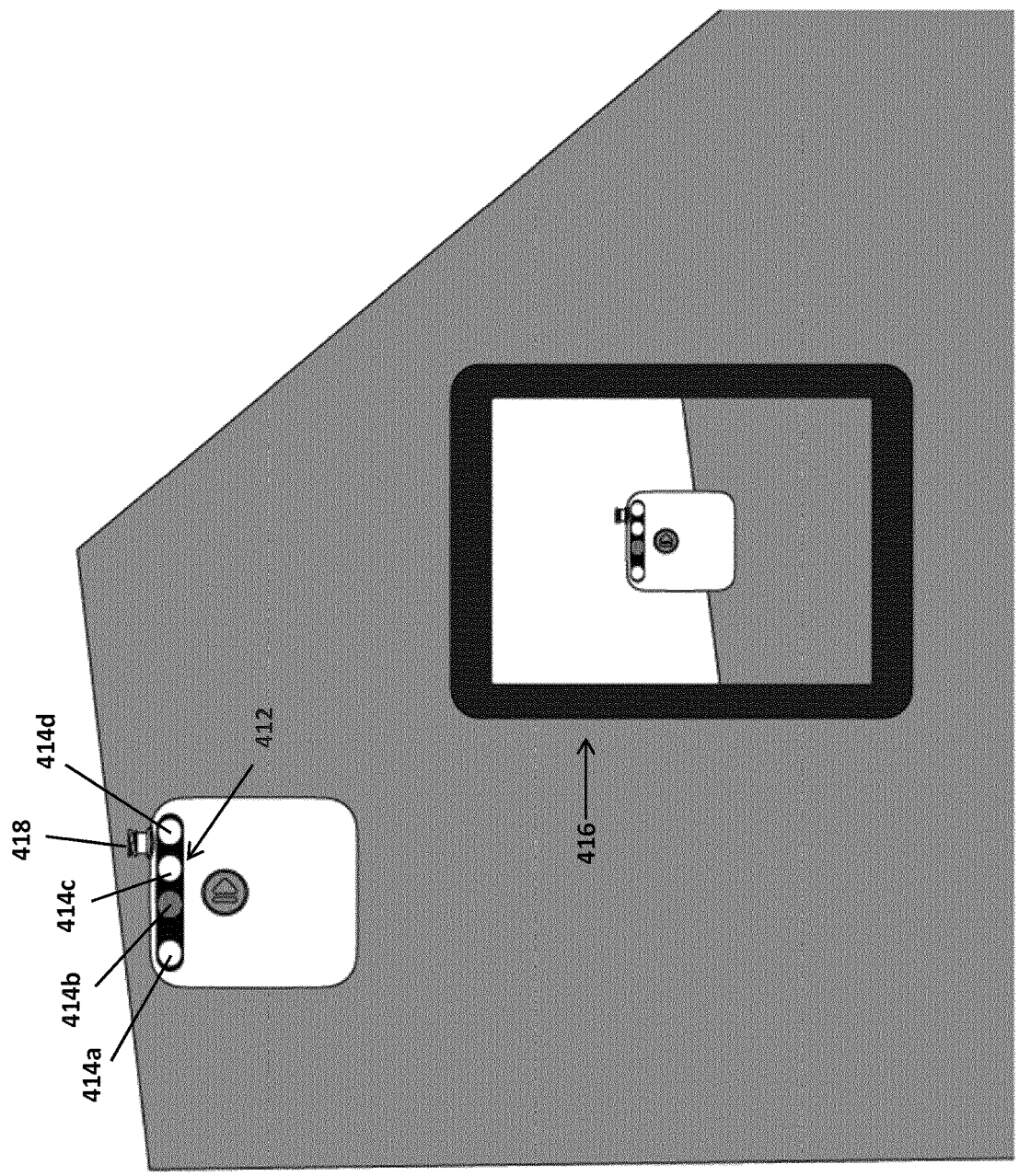
Figure 4D:
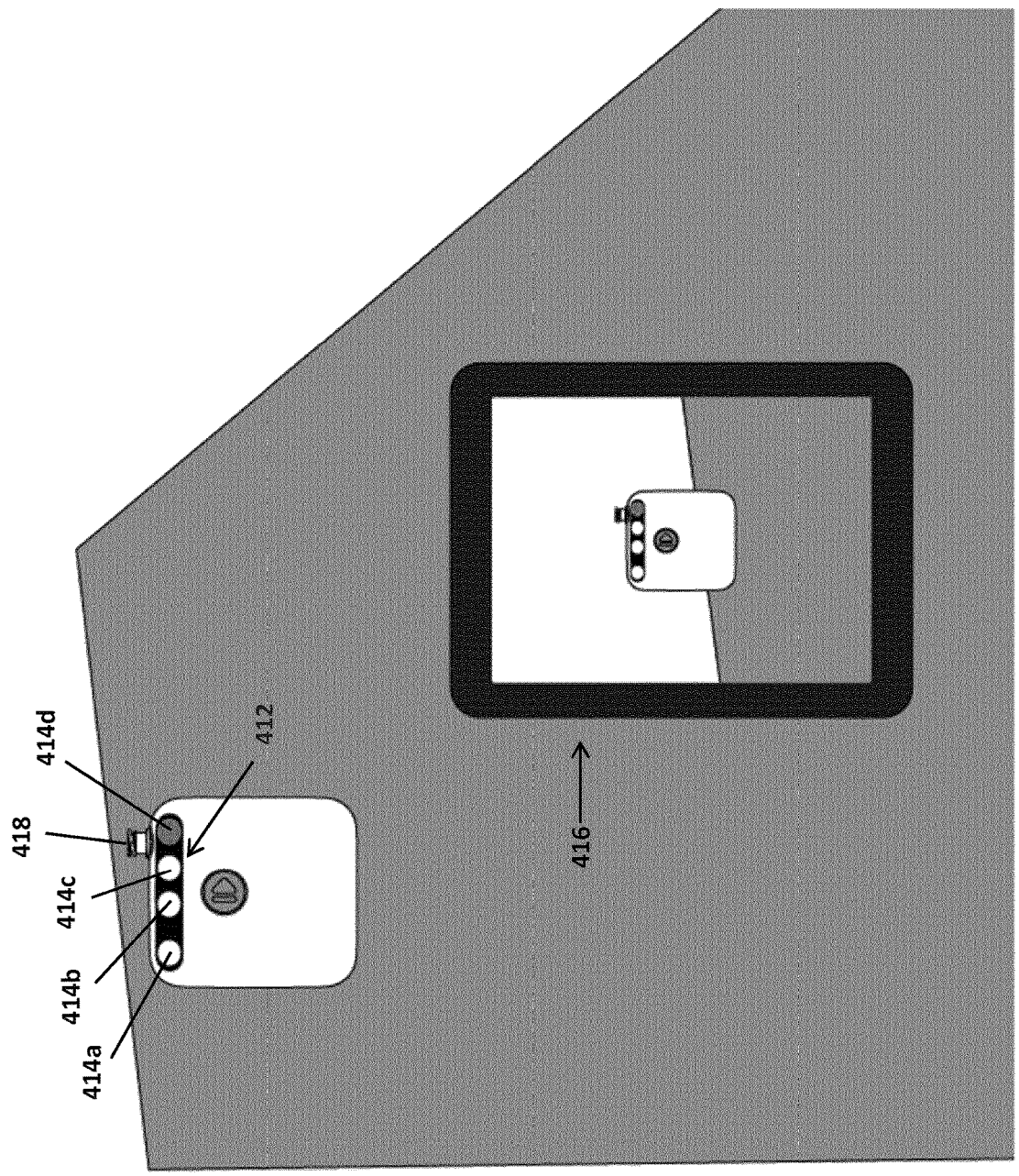
Figure 4E:
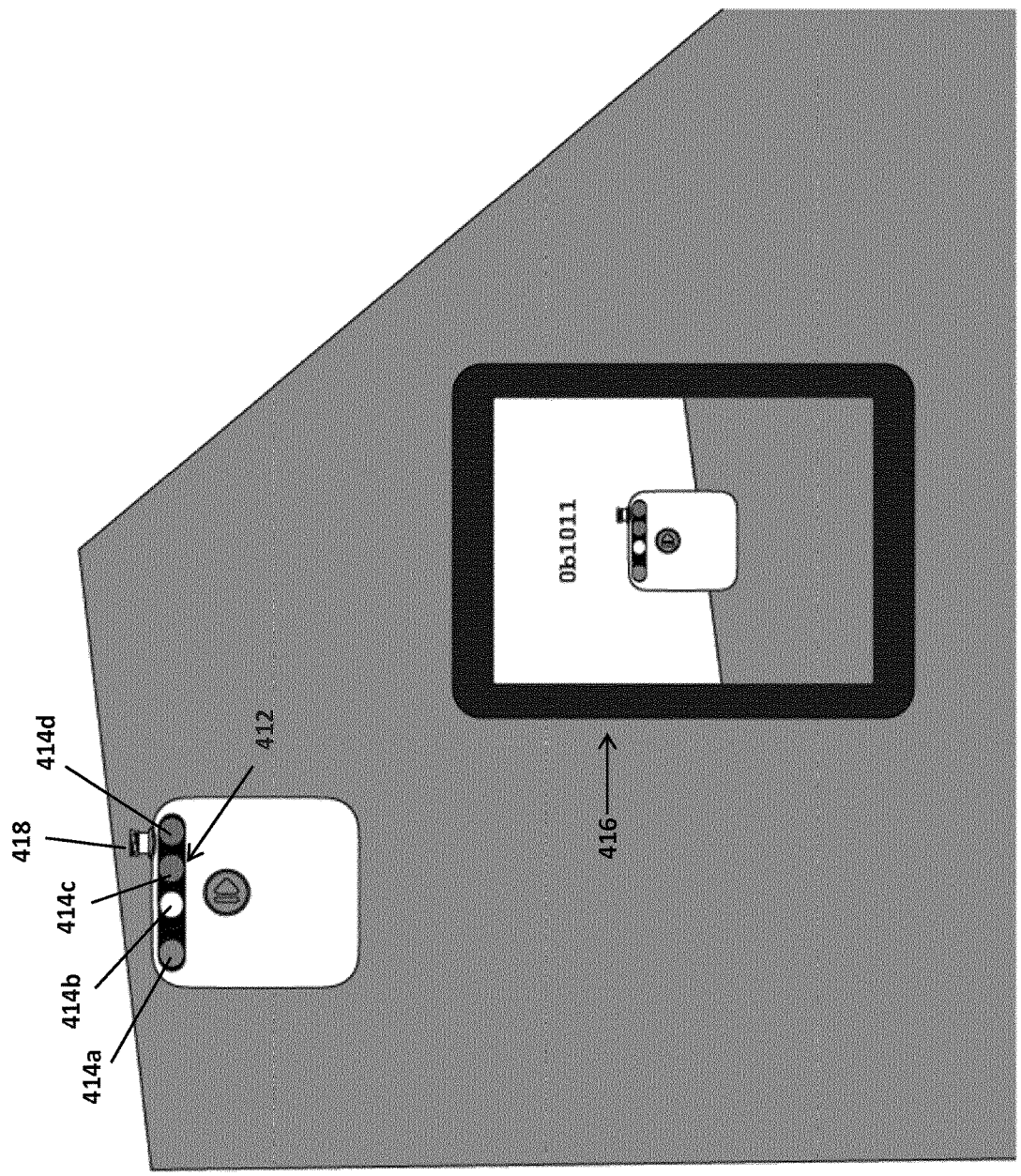
Figure 4F:
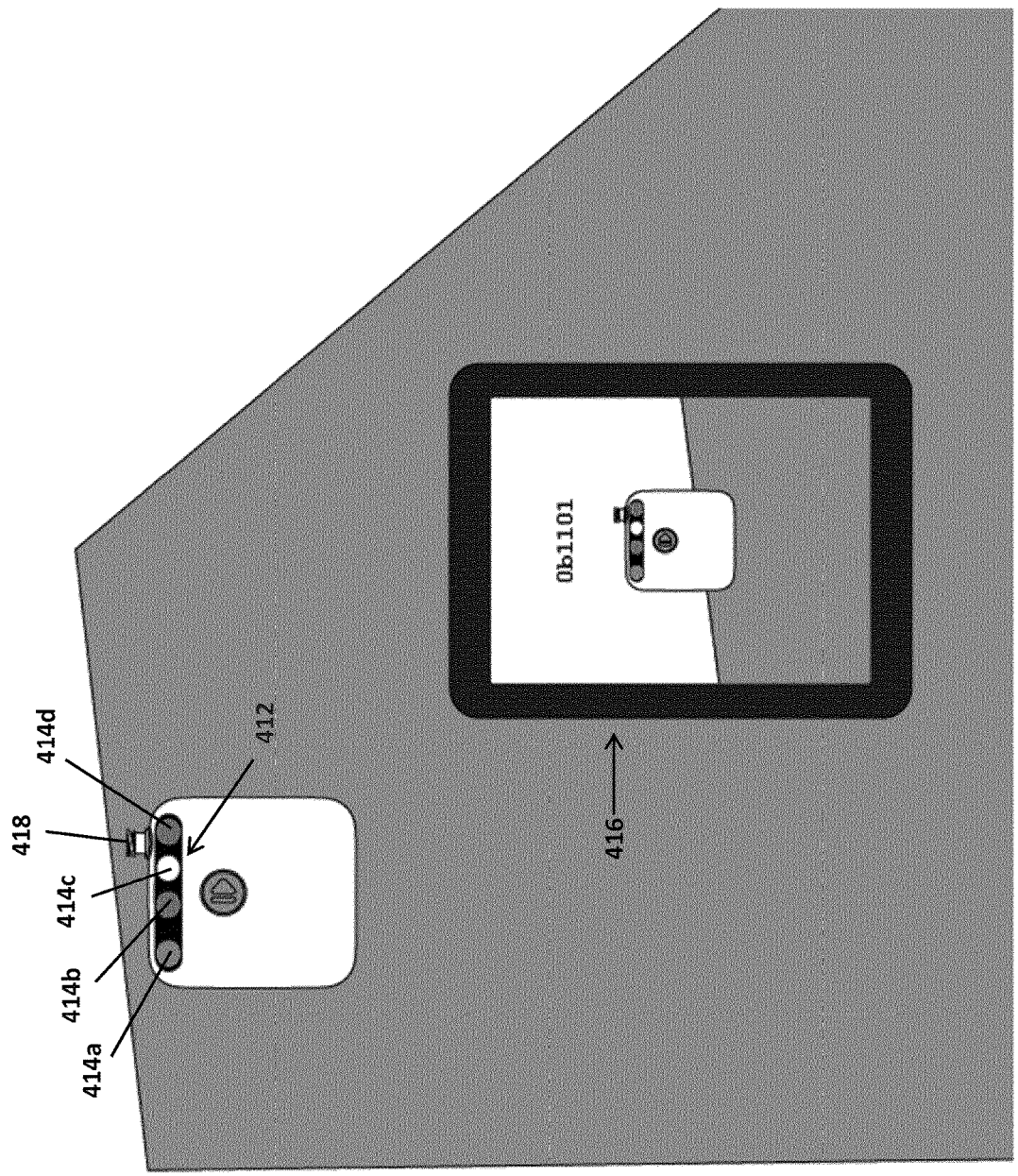

The indicators 414 can be multiple colors and one color indicator 414 and one color can denote different information than when another color of indicator 414 is illuminated. For example, one indicator 414a in the first position on the interface could illuminate in either a constant red or green color or can flash between a red color, green color, or no color throughout the time period the information is being transferred to the remote electronic device as illustrated in FIG. 4B. Additionally, the second, third, and fourth position indicators 414b, 414c, and 414d, respectively, can illuminate in either a constant red or green color or can flash between a red color, green color, or no color throughout the time period the information is being transferred similar to the first position indicator 414a. For example, FIG. 4C illustrates the second position indicator 414b illuminated while all other position indicators 414a, 414c, and 414d are not illuminated and FIG. 4D illustrates the fourth position indicator 414d illuminated while all other indicators 414a, 414b, and 414c are not illuminated. FIGS. 4E and 4F show multiple positions of the indicators 414 illuminated at the same time. In some embodiments, the interface can use more or less than 4 indicators to generate the pattern or communicate the status and/or information. The constant color, changing of colors, or the pattern of the change in color of all four indicators 414 can communicate different information about the system. To transfer or decode the information relating to the system being shown on the interface by the illumination of indicators 414a, 414b, 414c, and 414d, the remote detection device or electronic device 416 can be used.

In some embodiments, the electronic device can have a software preloaded to provide the necessary decoding or reading of the illumination pattern. The electronic device can include a camera (not shown) for providing images to the system of the illuminated indicators. The images of the indicators and the pattern of illumination can be utilized by the software which decodes the pattern to communicate a condition or information relating to the dressing or pump system. The camera can capture the images through a video or through multiple still images taken in periodic succession. For example, a clinician or medical professional can position the electronic device 416 so that the camera is facing the front of the wound dressing device. In some embodiments, a small fixture can be used with the electronic device and the dressing or pump system to position the camera at the appropriate position to capture the information. The fixture can be made out of cardboard, plastic, or other material that can provide appropriate support.

The application or software preloaded on the electronic device 416 can be accessed by the clinician. The clinician forces the indicators 414 on the dressing and pump system to go into a data transmission mode. The indicators 414 can transmit the data 4 bits at a time using the four indicators 414 as shown on the interface 412 in FIGS. 4A-F. As shown in FIGS. 4B, 4E and 4F, the interface 412 can communicate information using binary code corresponding to the illuminated indicators 414a-414d. For example, as is illustrated in FIG. 4B, indicator 414a is illuminated (or active), while indicators 414b, 414c, and 414d are not illuminated. This illumination pattern can correspond to a binary sequence 0b1000, which is communicated to the device 416. As another example, as is illustrated in FIG. 4E, indicators 414a, 414c, and 414d are illuminated while indicator 414c is not illuminated. This illumination pattern can correspond to a binary sequence 0b1011, which is communicated to the device 416. As yet another example, as is illustrated in FIG. 4F, indicators 414a, 414b, and 414d are illuminated while indicator 414c is not illuminated. This illumination pattern can correspond to a binary sequence 0b1101, which is communicated to the device 416. The communicated binary sequence can be associated with status and/or other information.

The electronic device 416 can use the received data to provide the clinician with a summary of the operation of the pump system and/or the dressing. For example, the electronic device can determine if the filter has been blocked, how well sealed the dressing is, or if the pump has been removed for long periods of time, duration and type of therapy delivered, any error encountered error conditions, and the like. Based on the status or information communicated about the system, a remedial action can be taken on the pump system or dressing. Such action can include a dressing change, a power source changed, pump output alteration, and/or any other modifications that can be made to the dressing to correct and/or alter in response to the indicated status or information obtained.

In some embodiments, electronic devices such as smartphones or tablets can have the capacity to capture less than or equal to about 40 bit/s to greater than or equal to about 1 Kbit/s. For example, the electronic device can capture about 4 bit/s to about 8 bit/s, about 8 bit/s to about 20 bit/s, about 20 bit/s to about 40 bit/s, about 40 bit/s to about 100 bit/s, about 100 bit/s to about 300 bit/s, about 300 bit/s to about 600 bit/s, about 600 bit/s to about 800 bit/s, about 800 bit/s to about 1 Kbit/s, or faster than about 1 Kbit/s. In some embodiments, the electronic device can capture the data at 40 bit/s. A download of the basic data relating to the summary of the therapy with the methods described above can take only a few seconds.

With reference to the pump system 100 illustrated in FIGS. 1-2 and FIGS. 4A-F, the pump system 100 can include one or more user input features, such as button 116, designed to receive an input from the user for controlling the operation of the pump system 100. In the embodiment shown, a single button is present which can be used to activate and deactivate the pump system 100 and/or control other operating parameters of the pump system 100. For example, in some embodiments, the button 116 can be used to activate the pump system 100, pause the pump system 100, clear indicators such as indicators 114, and/or be used for any other suitable purpose for controlling an operation of the pump system 100 (e.g., by sequentially pushing on the button 116). The button can be a push style button that can be positioned on an outside, front surface of the housing. In other embodiments, multiple input features (e.g., multiple buttons) can be provided on the pump system 100. Additionally, the button can be used to force the pump system to go into data transmission mode for communicating the data to the electronic device 416 described with reference to FIGS. 4A-F. By holding the button 116 for several seconds or by pressing button 116 several times, the user can cause the interface to go into the data transmission mode.

Additional Embodiments of Negative Pressure Wound Therapy System

In some embodiments, the button 116 can be designed to eliminate or at least reduce the potential for leakage around the button 116. In some embodiments, a peripheral portion of the button 116 can be placed in an interference fit with a surrounding lip of the outer housing 102. In some embodiments, the entirety or portions of the button 116 can be formed of a deformable material capable of forming a relatively hermetic seal when abutted against a surface, such as rubber, silicon, or any other suitable material.

Figure 5:
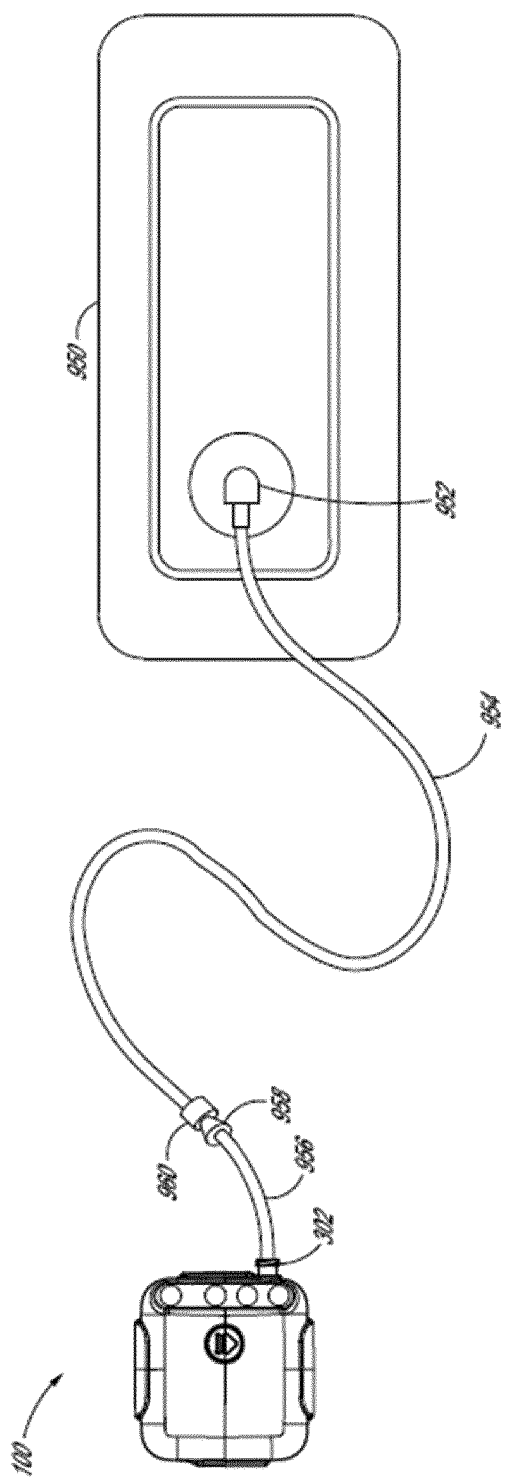
FIG. 5 is a top view of an embodiment of a pump system attached to a wound dressing.

In some embodiments, the pump system 100 can include a connector 302 for connecting a tube or conduit to the pump system 100. For example, as shown in FIG. 5, the connector 302 can be used to connect the pump system 100 to a dressing 950. As shown in the illustrated embodiment, the dressing 950 can include a port 952 for receiving an end of the conduit 954. In some embodiments, the conduit 954 can be connected directly to the connector 302 of the pump system 100. In some embodiments, such as that shown in FIG. 5, an intermediate conduit 956 can be used and attached to conduit 954 via a connector, such as a quick release connector 958, 960.

Figure 6:
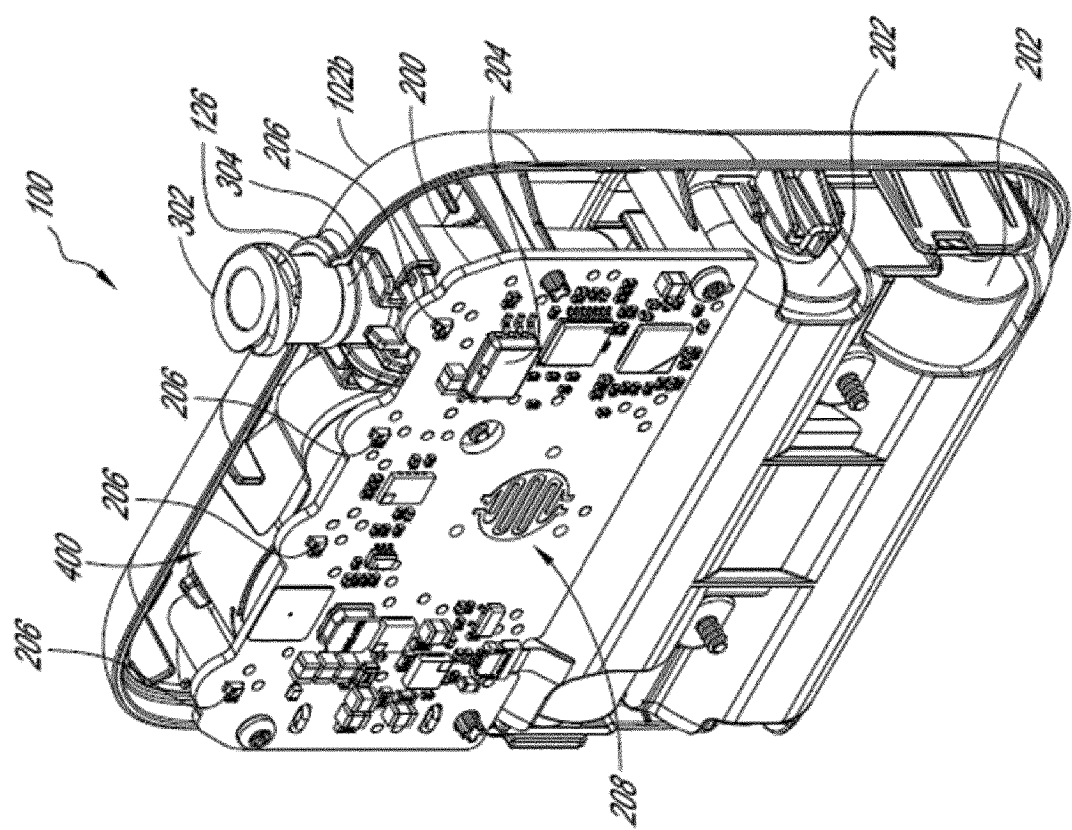
FIG. 6 is a front perspective view of the outer housing of FIG. 1, with a front portion of the outer housing removed to expose an embodiment of a circuit board and pump assembly.

FIG. 6 illustrates perspective views of an embodiment of a pump system 100 with portions of the outer housing 102 removed to expose an embodiment of a circuit board 200, an intake manifold 300, and a source of negative pressure such as a pump assembly 400.

The control board 200 can be designed to control the function of the pump system 100 such as the pump assembly 400. The control board 200, such as a printed circuit board assembly (PCBA), can be designed to mechanically support and electrically connect various electrical/electronic components of the pump system 100. For example, in some embodiments, the control board 200 can connect one or more batteries and/or other power sources 202 to the pump assembly 400 to provide power to operate the pump assembly 400. In some embodiments, the control board 200 can include a pressure monitor 204. The pressure monitor 204 can be supported by the control board 200 and can be designed to monitor a level of pressure in a fluid flow passageway. The control board 200, in conjunction with the pressure monitor 204, can be designed to protect the pump assembly 400 from exceeding a predefined threshold pressure and/or can be designed to maintain a target pressure at the wound.

The circuit board 200 can be designed to cut power to the pump assembly 400 if the pressure reading reaches a predetermined value, and be designed to resume when the pressure level drops below the predetermined value or a second predetermined value that can be higher or lower than the first predetermined value. Additionally, the control board 200 can be programmed to prevent such over-pressurization.

In some embodiments, the control board 200 can include indicator lights, audible alarms, and/or a combination of such features. For example, in some embodiments, the control board 200 can include indicator lights in the form of one or more LEDs 206. As discussed above in connection with FIGS. 1-2, the one or more LEDs 206 can be used to illuminate one or more indicators 114 of the interface 112 on the outer housing 102. In some embodiments, each LED 206 can correspond to one or more indicators 114. In some embodiments, the control board 200 can have one or more features 208 (e.g., pressure sensitive switch(es)) to receive an input from the control button 116.

In any of the embodiments disclosed herein, the control board 200 can be a flexible circuit board and/or can have one or more flexible components. A flexible circuit board is generally a patterned arrangement of printed circuitry and components that utilizes flexible based material with or without flexible overlay. These flexible electronic assemblies can be fabricated using the same components used for rigid printed circuit boards, but allowing the board to conform to a desired shape (flex) during its application. In their simplest form, flexible circuits are PCBs made of materials that allow for a non-planar positioning within the end product. Typical materials a polyimide-based, and can go under trade names such as Kapton (DuPont). Additionally, any of the control boards or controllers disclosed herein can have a combination of flexible and rigid substrates laminated into a single package.

Figure 8:
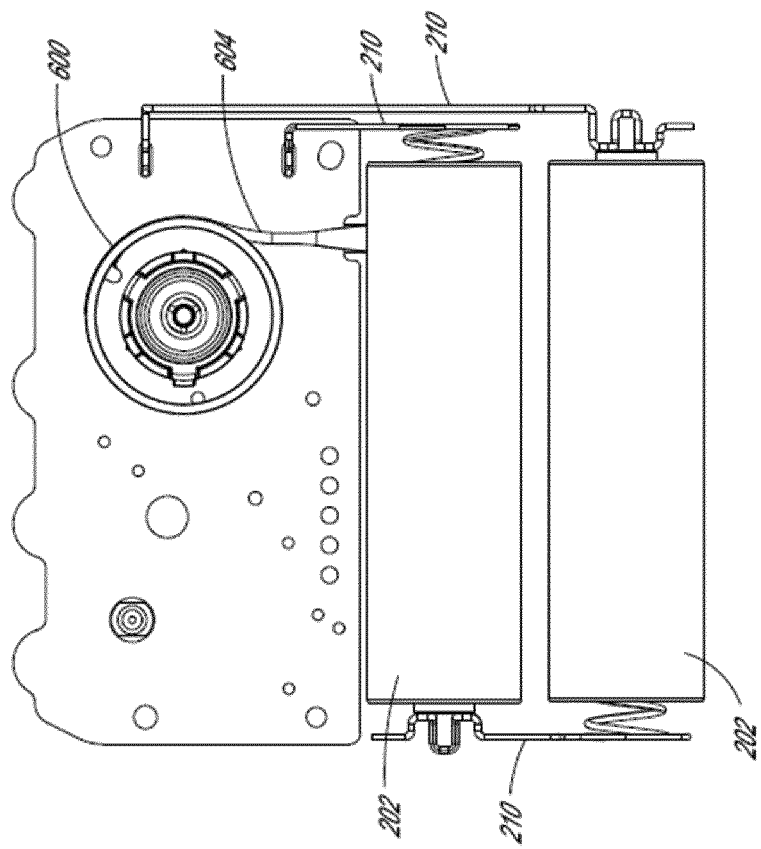
FIG. 8 is a rear view of the circuit board of FIG. 6.
Figure 7:
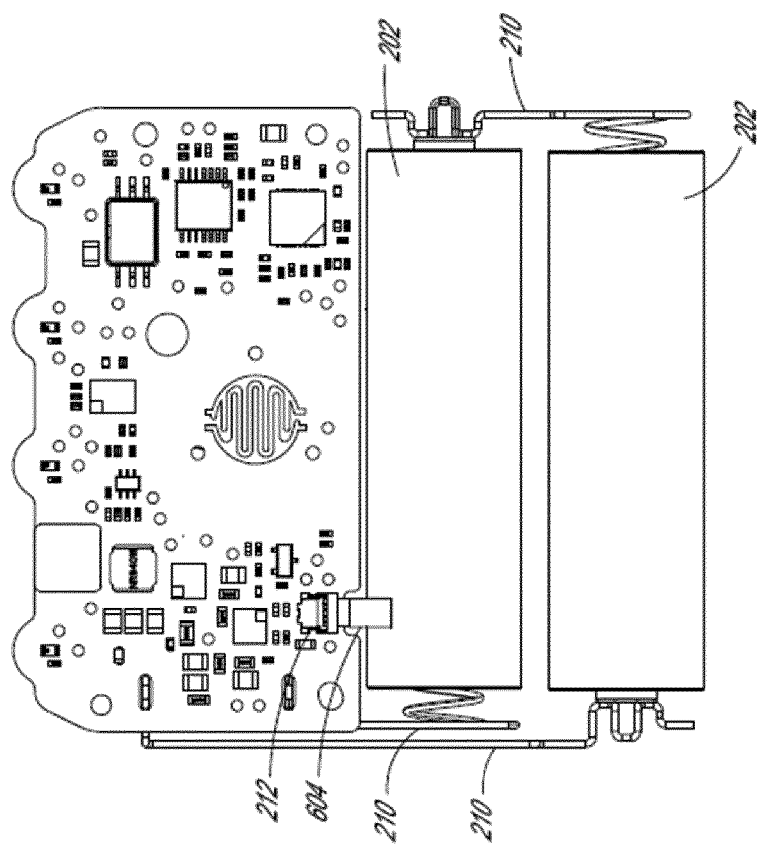
FIG. 7 is a front view of the circuit board of FIG. 6.

FIGS. 7-8 are various views illustrating wiring of the pump system 100 within the outer housing 102. As shown in the illustrated embodiment, the pump system 100 can include terminals 210 for connecting the circuit board 200 to a power source, such as batteries 202. The circuit board 200 can route power from the power source to the coil 600 via an electrical conduit 604 attached to a connector 212 of the circuit board 200. In some embodiments, the electrical conduit 604 can be a flexible printed circuit (FPC) to facilitate assembly. In some embodiments, the electrical conduit 604 can be connected directly to the coil 600. For example, the ends of the FPC corresponding to a positive and negative terminal can be attached, such as via soldering and/or via adhesives, to ends or terminals of the coil 600. Additionally, a control board of the pump assembly can have one or more fuses to protect against overpower conditions or surge power conditions.

Figure 9:
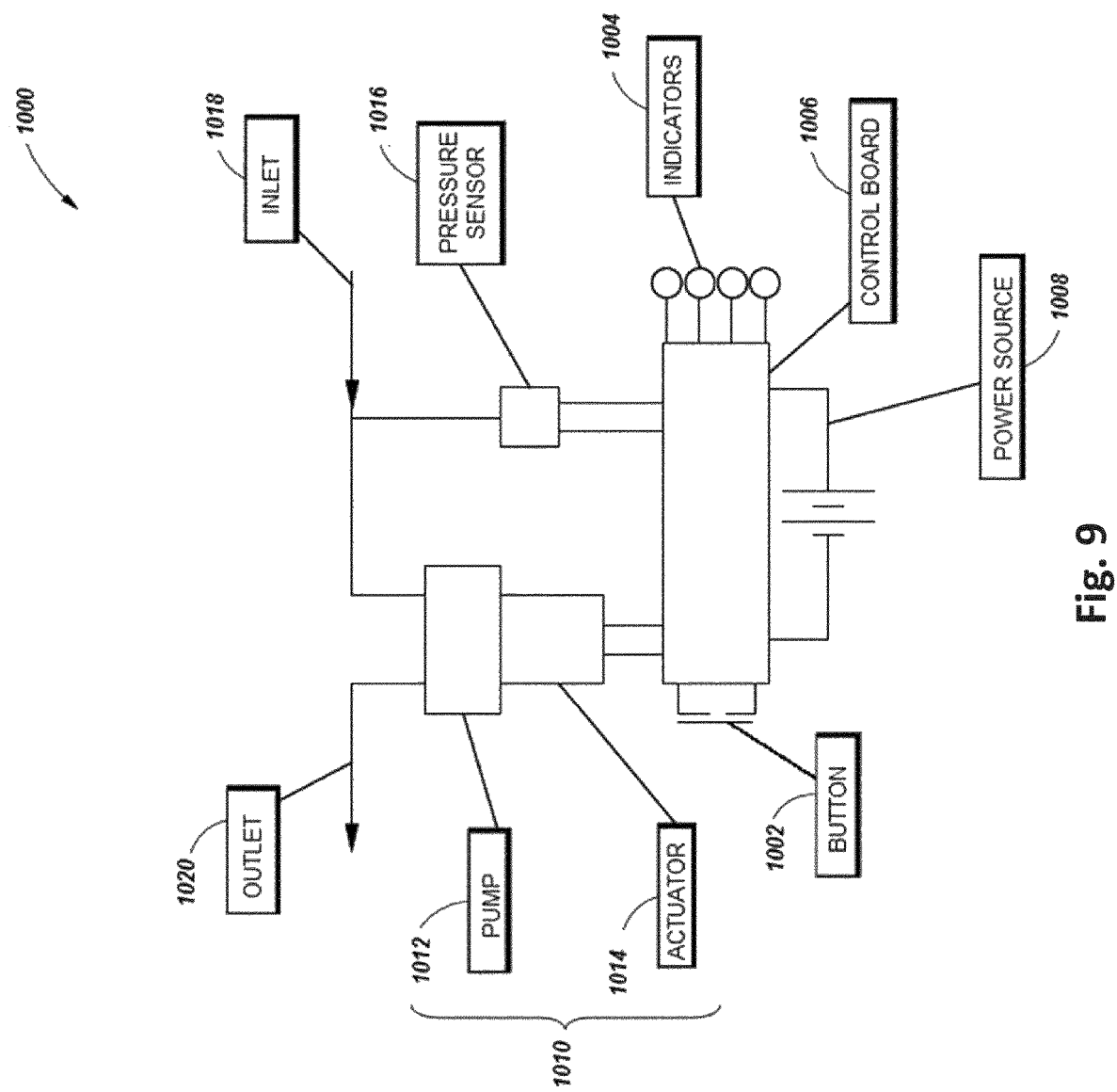
FIG. 9 is a schematic of an embodiment of a pump system.

FIG. 9 illustrates a schematic of an embodiment of a pump system 1000. In some embodiments, the pump system 1000 can have any of the same or similar components, features, materials, sizes, configurations, and other details of any other pump system embodiments disclosed or incorporated by reference herein, including the embodiment of the pump system 100 described above. In some embodiments, the pump system 1000 can be miniaturized and portable, although larger conventional portable or non-portable (e.g., wall suction) pumps can also be used.

As shown in the illustrated embodiment, the pump system 1000 can include a switch or a button 1002, one or more indicators 1004, and a control board 1006. The button 1002 and/or the one or more indicators 1004 can be in electrical communication with the control board 1006. As is explained in further detail below, in some embodiments the button 1002 can be used for any suitable purpose for controlling an operation of the pump system 1000. For example, button 1002 can be used to activate the pump system 1000, pause the pump system 1000, clear system indicators 1004, and/or be used for any other suitable purpose for controlling an operation of the pump system 1000. Button 1002 can by any type of switch or button, such as a touchpad, touch screen, keyboard, and so on. In some embodiments, the button 1002 can be a press button. For example, the button 1002 can be similar to button 116 of pump system 100.

In some embodiments, the one or more indicators 1004 can indicate one or more operating and/or failure conditions of the pump system 1000. In some embodiments, each of the one or more indicators 1004 can provide an indication regarding a different operating and/or failure condition. For example, an active (e.g., lit) indicator 1004 can represent normal operation. Another indicator 1004, for example a dressing indicator, can provide an indication as to presence of leaks in the system. For example, an active (e.g., lit) dressing indicator can represent a leak. Another indicator 1004, for example a dressing capacity indicator, can provide an indication as to the remaining fluid capacity of a dressing. For example, an active (e.g., lit) dressing capacity indicator can represent that the dressing is at or nearing capacity. Another indicator 1004, such as a battery indicator, can provide an indication as to remaining capacity or life of a power source, such as batteries. For example, an active (e.g., lit) battery indicator can represent a low capacity. In some embodiments, an indicator 1004 can represent a combination of the above operating and/or failure conditions of the pump system 1000 and/or other operating and/or failure conditions.

With continued reference to the embodiment of pump system 1000 illustrated in FIG. 9, in some embodiments, the one or more indicators 1004 can be icons. For example, the one or more indicators 1004 can be similar to the icons 114 of pump system 1004 and can be activated (e.g., lit) via an illumination source such as LEDs 206 of pump system 100. In some embodiments, the one or more indicators 1004 can be of a different color, two different colors (e.g., two indicators can share the same color), or same color. Although the pump system 1000 can include four icons and a push play/pause button, other configurations, locations, and types of indicators, alarms, and switches can alternatively be used. In some embodiments, the pump system 1000 can include visual, audible, tactile, and other types of indicators or alarms configured to signal to the user various operating conditions. Such conditions include system on/off, standby, pause, normal operation, dressing problem, leak, error, and the like. The indicators can include speakers, displays, light sources, etc., and/or combinations thereof.

As shown in the illustrated embodiment, the pump system 1000 can be powered by a power source 1008 such as a battery power cell. The pump system 1000 can also include a source of negative pressure 1010, such as a pump assembly having a pump 1012 powered by an electric motor 1014, and a pressure sensor 1016, such as pressure monitor 204 of pump system 100. In some embodiments, the pump system 1000 can include an inlet 1018 to connect the pump system 1000 to a wound dressing. For example, in some embodiments, the inlet 1018 can be a connector for connecting the inlet 1018 to a conduit which is in fluid communication with a wound dressing. The connector can be similar to connector 302 of pump system 100. The pump 1012 can be connected to an outlet 1020. In some embodiments, the outlet 1020 can vent air to the atmosphere. In some embodiments, a filter (not shown) can be interposed between the outlet and the atmosphere. The filter can provide filtration of the air prior to venting to the atmosphere. In some embodiments, the filter can be a bacterial filter, odor filter, etc. or any combination thereof. In some embodiments, a dampening component (not shown), such as a noise dampening component, can be interposed between the outlet and the atmosphere. The dampening component can reduce the noise generated by the pump system 1000 during operation.

In some embodiments, the pump system 1000 can include a valve (not shown), such as a one-way valve, in a flow passage between the wound dressing and an inlet of the pump 1012. The valve can help maintain a level of negative pressure when the pump 1012 is not active. In some embodiments, the valve can help avoid leaks. The valve can also help prevent fluids and/or exudate aspirated or removed from the wound from entering the pump system 1000.

Figure 10:
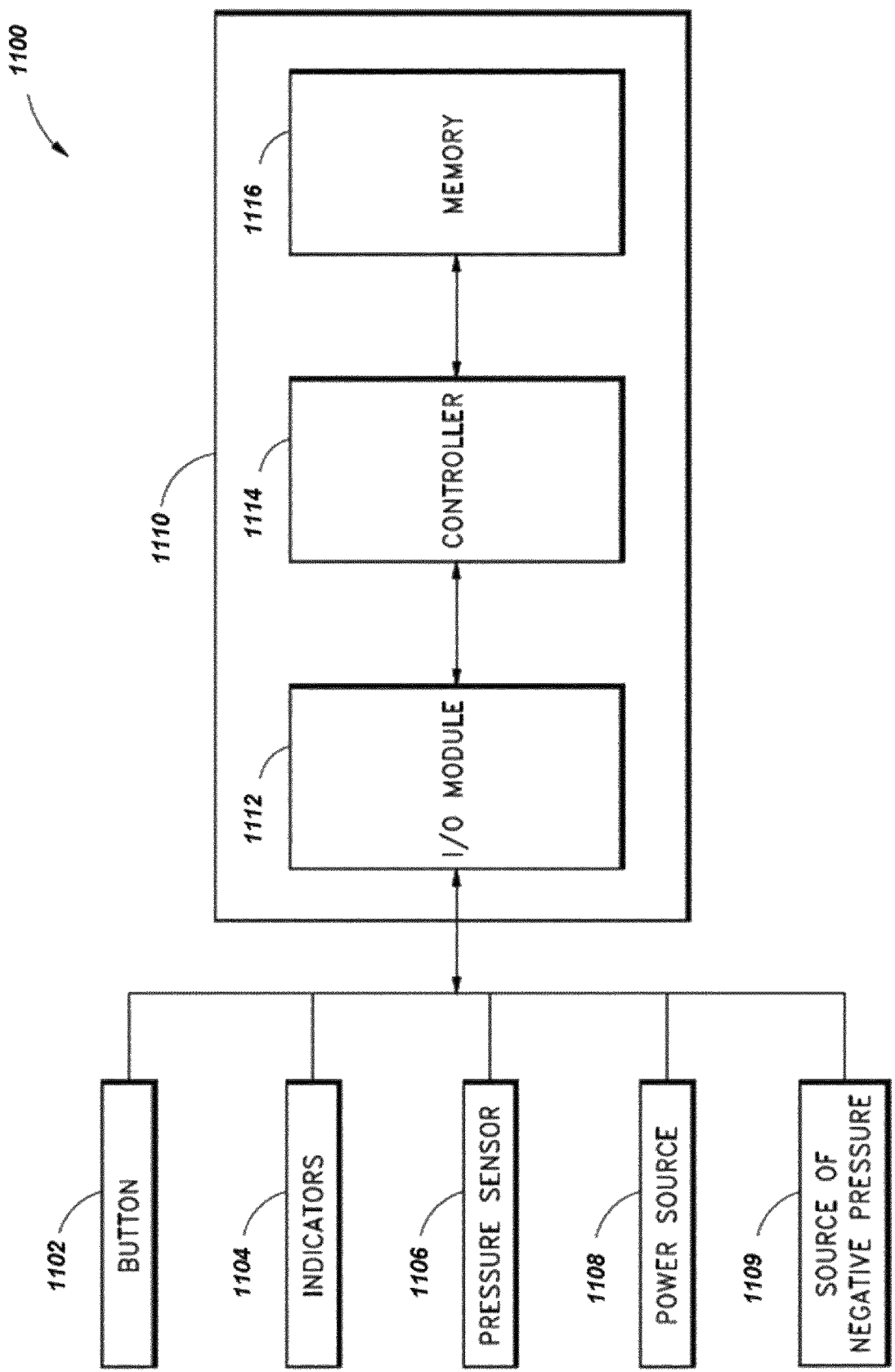
FIG. 10 is a schematic of another embodiment of a pump system.

FIG. 10 illustrates an electrical component schematic of a pump system 1100 according to an embodiment. In some embodiments, the pump system 1100 can have any of the same or similar components, features, materials, sizes, configurations, and other details of any other pump system embodiments disclosed or incorporated by reference herein, including the embodiment of the pump system 100, 1000 described above. Pump system 1100 can include one or more buttons 1102, one or more indicators 1104, one or more pressure sensors 1106, power source 1108, a source of negative pressure 1109, and/or a module 1110. In some embodiments, the one or more buttons 1102, one or more indicators 1104, one or more pressure sensors 1106, power source 1108, and/or source of negative pressure 1109 can be similar to button 1002, indicators 1004, pressure sensor 1016, power source 1008, and/or source of negative pressure 1010 of pump system 1000. Module 1110, which can be a control board (e.g., PCBA), can include an input/output (I/O) module 1112, controller 1114, and memory 1116. In some embodiments, module 1110 can include additional electric/electronic components, for example, fuse or fuses. The controller 1114 can be a microcontroller, processor, microprocessor, etc. or any combination thereof. For example, the controller 1114 can be of the STM8L MCU family type from ST Microelectronics, such as STM8L 151K6U6TR, or of MC9S08QE4/8 series type from Freescale, such as MC9S08QE4CWJ. Preferably, the controller 1114 is a low power or ultra low power device, but other types of devices can alternatively be used. In some embodiments, the controller 1114 can be configured to operate the negative pressure source 1109 (for example, based on pressure sensed by the one or more pressure sensors 1106) and the indicators 1104. Memory 1116 can include one or more of volatile and/or nonvolatile memory modules, such as one or more of read-only memory (ROM), write once read many memory (WORM), random access memory (e.g., SRAM, DRAM. SDRAM, DDR, etc.), solid-state memory, flash memory, Magnetoresistive random-access memory (MRAM), magnetic storage, etc. or any combination thereof. Memory 1116 can be configured to store program code or instructions (executed by the controller), system parameters, operational data, user data, etc. or any combination thereof.

Energy Harvesting for Providing Power to Negative Pressure Wound Therapy System

The pump system 1100 can be powered by a power source or generator 1108, which can comprise one or more disposable or rechargeable batteries, power from mains, or other embodiments as described herein. The power source or generator 1108 can be internal or external to the system 1100.

Alternatively, the pump system 1100 can be powered by a power source 1108 other than batteries, such as an energy generator (or energy harvester). The pump system 1100 can utilize the energy harvesters as the power source 1108 to stay charged. The energy harvester can be in contact with the patient's skin and can utilize the temperature differential between the patient's skin and the atmosphere to generate the energy to power the pump system as well as other components.

The pump system 1108 can be worn by the patient during use with the dressing assembly. The pump system 1108 can be worn on the patient's wrist, waistband, arm, leg, or clipped to any of the patient's clothing. The pump system worn by the patient can be positioned to allow the pump system to be in contact with the patient's skin. In some embodiments, the pump system 1108 described herein can be a pump external to a wound dressing positioned at a location remote from the applied wound dressing. In some embodiments, the pump system 1108 and/or other electronic components described herein can be positioned on, adjacent to, or integrated within a wound dressing positioned over a wound of a patient. Body worn electrical devices such as pump systems 1100 have lifespans limited by their batteries. Usually a significant proportion of the device is made up of its battery. Alternative power sources have been considered such as energy harvesting. Although energy harvesting is possible, the components have been found to be bulky or have very low power outputs. Some medical devices use large energy harvesters to stay charges in devices such as medical alert transmitters. These can be physical weights that move through magnetic fields to generate energy and are of very low power and efficiency. Plug-in, inductive charging, or rechargeable batteries are also possible but require user action and inconvenience. This is equally true of replacing batteries. The continuous operation of energy harvesting also mitigates many usability engineering issues and user errors.

The use of an energy harvester of small size as a power source 1108 eliminates these issues and potentially gives unlimited duration of operation for a device. The size and weight of the harvester would be defined by the peak power requirement, not the capacity requirement and is therefore ideally suited to low or medium current applications over long durations. As such, Quantum well energy harvesting has been identified as a method for energy generation.

A pump and dressing system can be powered by a power source 1108 that utilizes harvesting of energy from a patient or user of the wearable device. The power source can comprise an energy harvester including a first surface or side in contact with a skin surface of a patient and a second surface or side in contact with the atmosphere. The pump and dressing system can be worn or positioned on the body of the patient to allow positioning of the energy harvester in contact with the patient's skin. A silicon chip harvester such as a Quantum well, Quantum dot, or other device can be used as the energy harvester to power electrical devices using the temperature differential between a patient's skin and the atmosphere.

The harvester can include a doped silicon matrix used to constrain electrons in a 'well' from which they escape when their quantum energy state increases due to heat input from the heat source. Once the electron leaves the 'well' it drops back to a lower quantum energy state by emitting the heat to the heat sink (cold sink). However, due to the matrix the electron cannot drop back into the well. The well therefore is an area of positive charge relative to the matrix and a new electron is drawn into the 'bottom' of the well. The process repeats, generating a current. The well acts as a one-way valve for the electrons and the fact that the energy can only be absorbed by the electron in quanta acts in a similar way to a piston or diaphragm acting on a process fluid.

The harvester includes a hot side that, when in use, is in contact with the patient's skin and a cold side that is in contact with the atmosphere. The harvester can be connected to the dressing and pump system and attached to the patient's skin at the dressing or pump site. In other embodiments, the harvester is a separate entity remote from the dressing or pump units. The remote harvester can be connected to the dressing and pump system by a tail or umbilical that can be placed in a more comfortable position on the body and/or one that would generate a higher temperature differential. The harvester may be stuck or adhered on to the skin or incorporated into a sock, belt, band etc.

In some embodiments, the power source can include an approximately 1 $cm^2$ to 6 $cm^2$ harvester with a hot side in contact with the patient's skin and a cold side in contact with the atmosphere in connection with a dressing and pump system. In some embodiments, the harvester can generate approximately 5-200 mW (for example, approximately 6-200 mW) to a dressing powering a DRUM NPWT pump also within the dressing. In some embodiments, the harvester can generate approximately 100-200 mW to a dressing powering a DRUM NPWT pump (or any other suitable pump, such as a peristaltic pump, voice coil pump, piezoelectric pump, etc.) also within the dressing. In some embodiments, the harvester can generate approximately 100-200 mW to a dressing powering a grid of Ultrasonic oscillators within the dressing. One or more small elements or harvesters can be incorporated into the dressing or pump system with a hot side in contact with a patient's skin and a cold side to the atmosphere that act as energy harvesters and power electrical elements such as sensors, Bluetooth, or Wi-Fi communication. Additionally, the power source may be used to power aspects of the dressing such as features of smart dressings. The power source for the smart dressings or other components can be similar to the power source described for use with the wearable pump system. In other embodiments, the energy harvester can be incorporated into a device that generates electrical potentials to trigger nerves for physiological effect such as generating compression-equivalence through tensing of muscles for increased blood flow. This can further stimulate the healing process within the wound area.

The electrical connection between the harvester and the pump or dressing system can be by physical electrical connection including electrical wires. In other embodiments, the electrical connection can be a wireless connection such as an inductive array. The mechanical connection can be made by any of multiple methods such as a silicone adhesive or magnetic connection.

The harvester can generate more energy than can be utilized by the system. In some embodiments, the harvester can also include a supercapacitor or other intermediate charge sink utilized to store charge from the harvester to allow greater power outputs at a lower duty cycle. For example, a 30 mW device can be powered by a 6 mW harvester at a 20% duty cycle. The harvester can be positioned on, incorporated into, or embedded within the dressing or pump. In some embodiments, the cool side of the harvester is thermally coupled to the dressing or device in order to act as a heat sink in the case the device does not utilize the full power rating of the harvester. In other embodiments, the harvester is incorporated into the outer surface of a wearable device with the hot side in contact with a plate that heats from light incident on it and the cold side to either atmosphere or the patient. The plate that heats from light incident on it can be made of photosensitive material or other material with good thermal conductivity. Alternatively, the heat source plate is implanted either within the skin or subcutaneously. This can include an embodiment where the harvester is in the form of a piercing or incorporated onto stitches.

Batteries or other energy storage devices can generate a hazard if the energy stored is liberated too quickly (such as a short or, in the case of lithium batteries, exposure to water). This hazard increases as the energy capacity goes up. Alternatively, an energy harvester as described herein is power limited and self-limiting. These features make the energy harvester a significantly lower hazard as a body-worn device. This can be particularly important for devices subject to IEC60601 standards.

The open-ended nature of the capacity means that 'wasteful' processes such as transmission of power over inductive arrays does not cut as badly into the energy budget. In some embodiments, such a system would allow there to be no physical electrical contact between the harvester and the powered device and could allow re-use of the harvester and/or ease recycling methodology.

Additionally, air shipment of lithium batteries is limited by the mass of lithium. Batteries also have specific disposal requirements while manufacturing and replacement utilizes materials and resources that are often not sustainable and have fluctuating prices. The harvester described above would have no similar prohibition. The open-ended operation of the harvester gives both an economic and environmental benefit.

Quantum dot energy harvesters have been tested successfully but are more complicated to make than Quantum well harvesters. The additional efficiency is not required for use in the dressing or pump systems described herein. The levels that are required in the described systems allow this less complicated technology to power many types of devices using only the temperature differential between the surface of the skin and the atmosphere, even the atmosphere under clothing.

Radio Frequency (RF) Harvesting for Providing Power to Negative Pressure Wound Therapy System Additionally, wearable devices such as NPWT pumps and smart dressings can be powered by other devices or methods. These methods and devices as discussed herein can eliminate the limitations of batteries. Batteries can create usability due to, for example, the weight, size, low life, and compliance with regulations such as Restriction of Hazardous Substances (RoHS) and Registration, Evaluation, Authorization, and Restriction of Chemicals (REACH) compliance.

Body worn electrical devices have lifespans limited by their batteries. Usually a significant proportion of the device is made up of its battery. Some energy harvesting can be bulky or can have very low power outputs. Plug-in or inductive charging or a rechargeable battery can also be used but they can require user action and inconvenience. This is equally true of replacing batteries. Therefore, the continuous operation of the harvesting device described herein can mitigate many usability engineering issues and user errors.

The use of an energy harvester of this small size eliminates these issues and can potentially give unlimited duration of operation for a device. In some embodiments, the size and weight of the harvester could be defined by the peak power requirement, not the capacity requirement. Therefore, the harvesting device as described herein can be ideally suited to low/medium current applications over long durations.

Batteries or other energy storage devices can generate a hazard if the energy stored is liberated too quickly (such as a short or, in the case of lithium batteries, exposure to water). This hazard can increase as the energy capacity goes up. A harvesting device as described herein can have no stored energy unless a capacitor or battery is used as a backup storage. Even in this case the stored energy requirement would be far smaller than that of a simple battery and the energy storage compartment could be completely sealed to prevent water ingress. Therefore, the hazard can be significantly lower for a body worn device; particularly for devices subject to IEC60601.

The air shipment of lithium batteries can be limited by the mass of lithium. Harvesting devices described herein may not have this prohibition. Batteries also have specific disposal requirements while manufacturing and replacement utilizes materials and resources that are often not sustainable and have fluctuating prices. The open-ended operation of the harvesting device can have both an economic and environmental benefit.

In some embodiments, a radio frequency (RF) energy harvesting device can be used to power components of a negative pressure therapy system and/or dressing. Crystal radios may not require a battery or power source. Instead, a crystal radio can utilize the RF signal to power devices such as a small earpiece or other speaker. Radio frequency can include a rate of oscillation in the range of around 3 kHz to 300 GHz. This range corresponds to the frequency of radio waves, and the alternating currents which carry radio signals. One or more aerials, transducers, and/or antennas can be used to pick up and harness the RF power similar to a crystal radio receiver. Additionally, a rectified antenna (also referred to as "rectenna") can be used to harvest energy. Rectennas can be used to derive direct current (DC) power from microwaves for beamed power uses. A rectenna is a special type of antenna that is used to convert microwave energy into direct current electricity. A rectenna can be used as a wireless power transmission system to transmit power by radio waves. That is, a rectenna can be used to generate power to provide power to the various components of the system and/or dressing.

Ambient frequency spectrum in most locales can have a lot of energy from a variety of sources (e.g., Wi-Fi, telecommunications systems, radio waves, light, etc.). In some embodiments, low power devices can utilize the ambient energy to operate without a dedicated source. In addition, if a small energy storage device is used, the storage device can allow for delivery of higher power to a device at lower duty cycles. Devices with a higher average power draw could use a dedicated base station that transmits RF power to aid charging. For example, the dedicated base station can either utilizing standard devices (e.g. Wi-Fi router) or a specific power transmission station designed for medium proximity energy transfer (e.g., a bedside charger designed for charging at a range of approximately 10 ft or less and transferring a day's worth of energy in approximately 5 hours or less). This base station could utilize a directed beaming of power to minimize waste.

In some embodiments, one or more aerials, transducers, and/or antennas can be built within, positioned within, and/or positioned on top of or adjacent to a dressing, into which the negative pressure wound therapy system may be embedded. The one or more aerials, transducers, and/or antennas can be used to pick up and harness RF power from ambient conditions and/or from an intentionally generated source, such as a dedicated base station. In some embodiments, unlike crystal radios, the harvesting device can attempt to harvest or generate energy on every frequency, rather than honing in on one frequency like crystal radios and thereby increase their energy harvesting ability. In other embodiments, the harvesting device can be configured to harvest energy on only one frequency or subset of frequencies.

In various embodiments, the harvesting device can be utilized as an alternative to and/or in addition to conventional batteries. The harvesting device can be incorporated into a dressing and/or integrated into another component of the negative pressure wound therapy system. In some embodiments, one or more aerials, transducers, and/or antennas built within a dressing can be used to pick up and harness RF power. The harvesting device can be equipped to pick up and harness power from ambient conditions. In some embodiments, the harvesting device can be equipped to pick up and harness power from an intentionally generated source. In some embodiments, the harvesting device can pick up and harness energy and power from ambient conditions and from an intentionally generated source. In some embodiments, the harvester device can harvest pre-existing energy or specifically generated charging station energy such as, for example, a home broadband router. The harvester device can pick up or harness environmental RF signal power such as RF signal power on spectrums on which signals are already broadcasted, like home router and mobile phone signal level. The harvester device can pick up or harness intentionally broadcasted RF signals. In some embodiments, these intentionally broadcasted RF signals can be on non-regulated spectrums.

In some embodiments, a higher frequency can allow for the device to use a smaller antenna. The antenna can be wired into the dressing or be placed on a portion of the dressing. In some embodiments, a longer antenna can be used. The longer antenna would allow a lower frequency to be used. The positioning of the antenna on the dressing or wired through the dressing allows for a longer antenna to be incorporated into the dressing or negative pressure wound therapy components such as the pump. In some embodiments, for example, a longer antenna can easily be wired through the dressing and be used to allow for lower frequencies to be detected and utilized. In some embodiments, more power can be generated at higher frequencies with the used of multiple antennas. In some embodiments, more power can be generated at higher frequencies with the used of multiple small antennas. In some embodiments, lower frequency radio signals (short wave radio) alone can be sufficient to keep the device running indefinitely.

Figure 11:
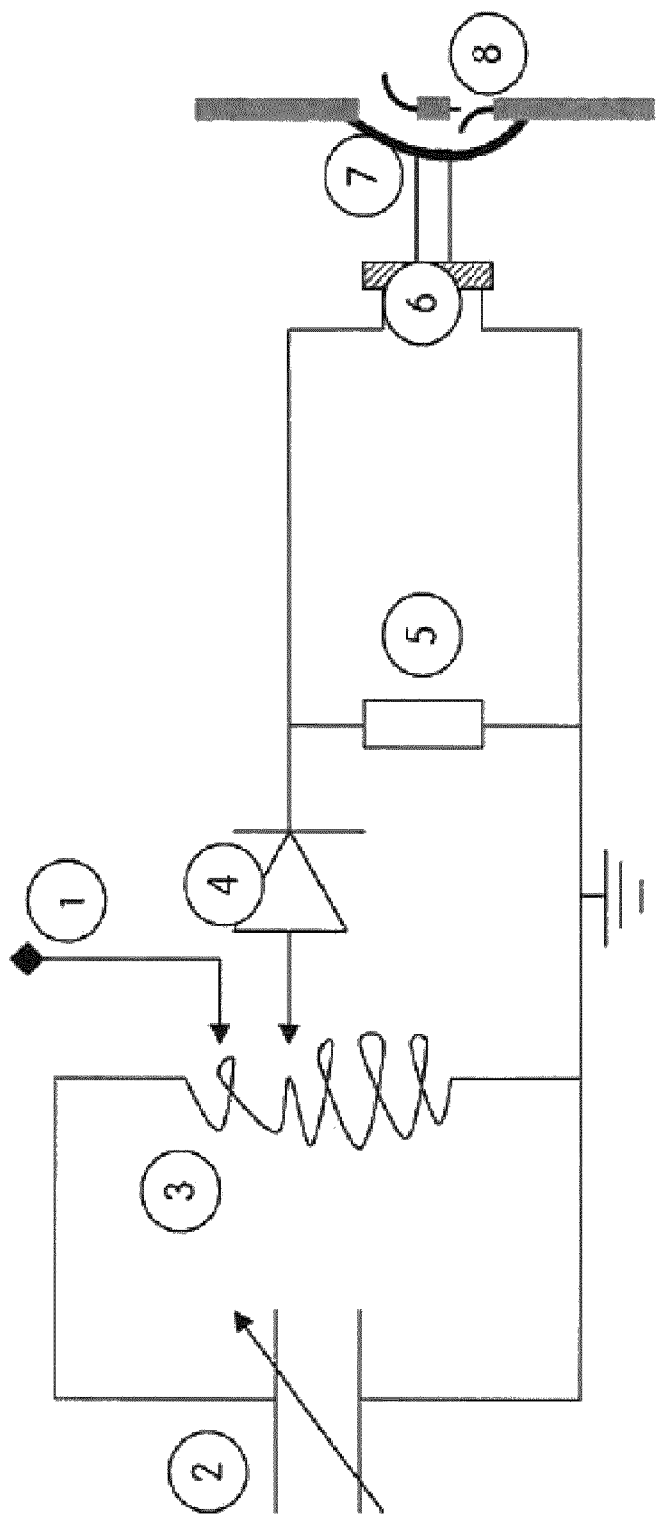
FIG. 11 is a circuit diagram of an energy harvester according to one embodiment.

FIG. 11 illustrates an embodiment of a circuit 1200 that can be used to harness RF energy and power components of the negative pressure therapy system. The circuit as shown in FIG. 11 can be positioned or placed within a housing of the negative pressure wound therapy system. The circuit 1200 illustrates an embodiment of a circuit that harvests or provides alternating current (AC). An antenna 1 may be woven into a dressing, positioned on the surface or within the device, or otherwise attached to the negative pressure therapy system as described herein. A variable capacitor 2 and variable inductor 3 are used to tune the circuit to a particular frequency or set of frequencies. The system also includes a diode 4 and resistor 5, which is connected to the diode 4 and ground. Harvested power can appear as alternating current across the resistor 5. The pump and other circuitry can be connected to the resistor 5. For example, a piezoelectric element 6 can be connected to the resistor 5. The piezoelectric element 6 is coupled to a diaphragm 7 which generates a swept volume with one or more one-way valves 8. The air movement through the pneumatic parts 7, 8 is then used to generate a pressure below ambient. In other embodiments, different vacuum pumps can be used, such as diaphragm pumps, voice coil pumps, and the like. Direct current can be obtained from the harvested alternating current using, for example, a suitable rectifier.

In some embodiments, two or more antennas can be used to harness and provide energy to the components of the negative pressure therapy system. In some embodiments, two identical antenna arrays could be mounted about half wavelength apart to capture the greatest potential difference. The peaks can be captured by the first array and the throughs can be captured by the second array. This arrangement can give the greatest captured power without needing an earth (or ground) connection and instead use a virtual ground.

Figure 12:
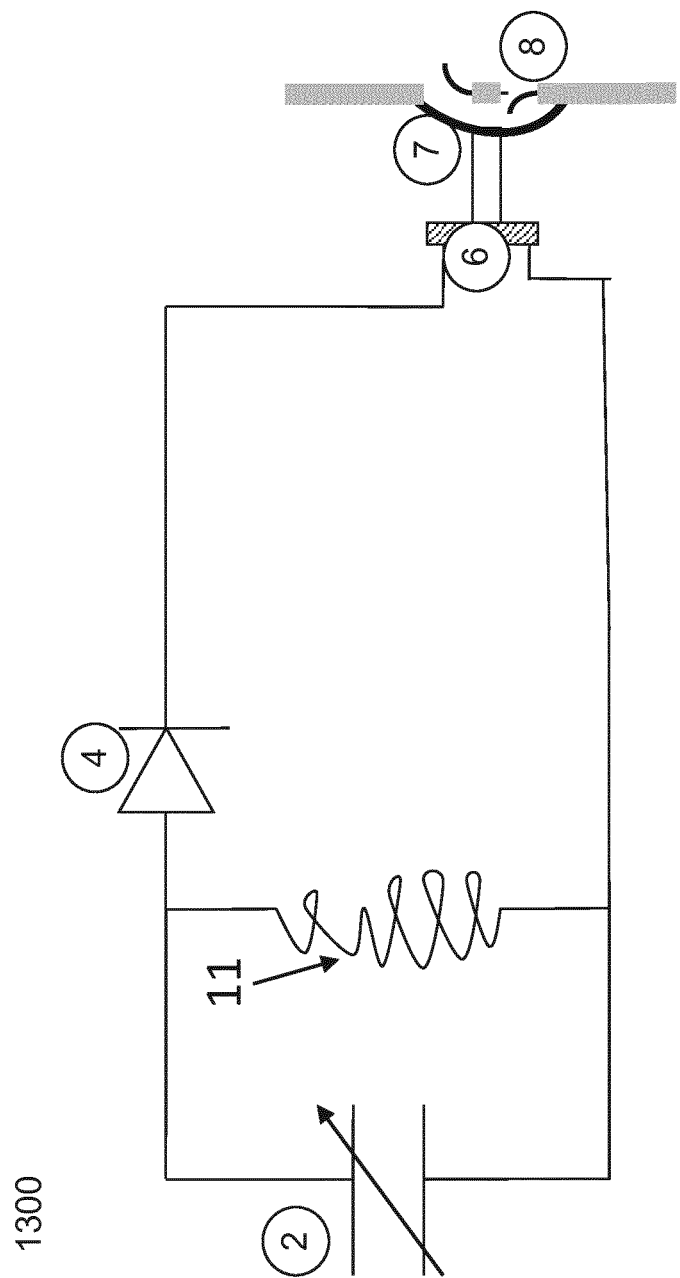
FIG. 12 is a circuit diagram of an energy harvester according to another embodiment.

FIG. 12 illustrates an embodiment of a circuit 1300, which is in some respects similar to the circuit 1200 illustrated in FIG. 11. Unlike circuit 1200, circuit 1300 of FIG. 12 includes a large coil 11 instead of the antenna 1 of FIG. 11. The coil 11 can be made of approximately 20 meters of 22 awg wire. Other lengths and wire gauges can be used to form the coil 11. The coil 11 can be used with the variable capacitor 2 and diode 4. Harvested power can appear as alternating current across the coil 11. Similar to FIG. 11, the piezoelectric element 6 can be connected across the coil 11 and be coupled to a diaphragm 7 which generates a swept volume with one or more one-way valves 8. The air movement through the pneumatic parts 7, 8 is then used to generate a pressure below ambient. Unlike circuit 1200, circuit 1300 does not require a ground connection for operation.

Figure 13:
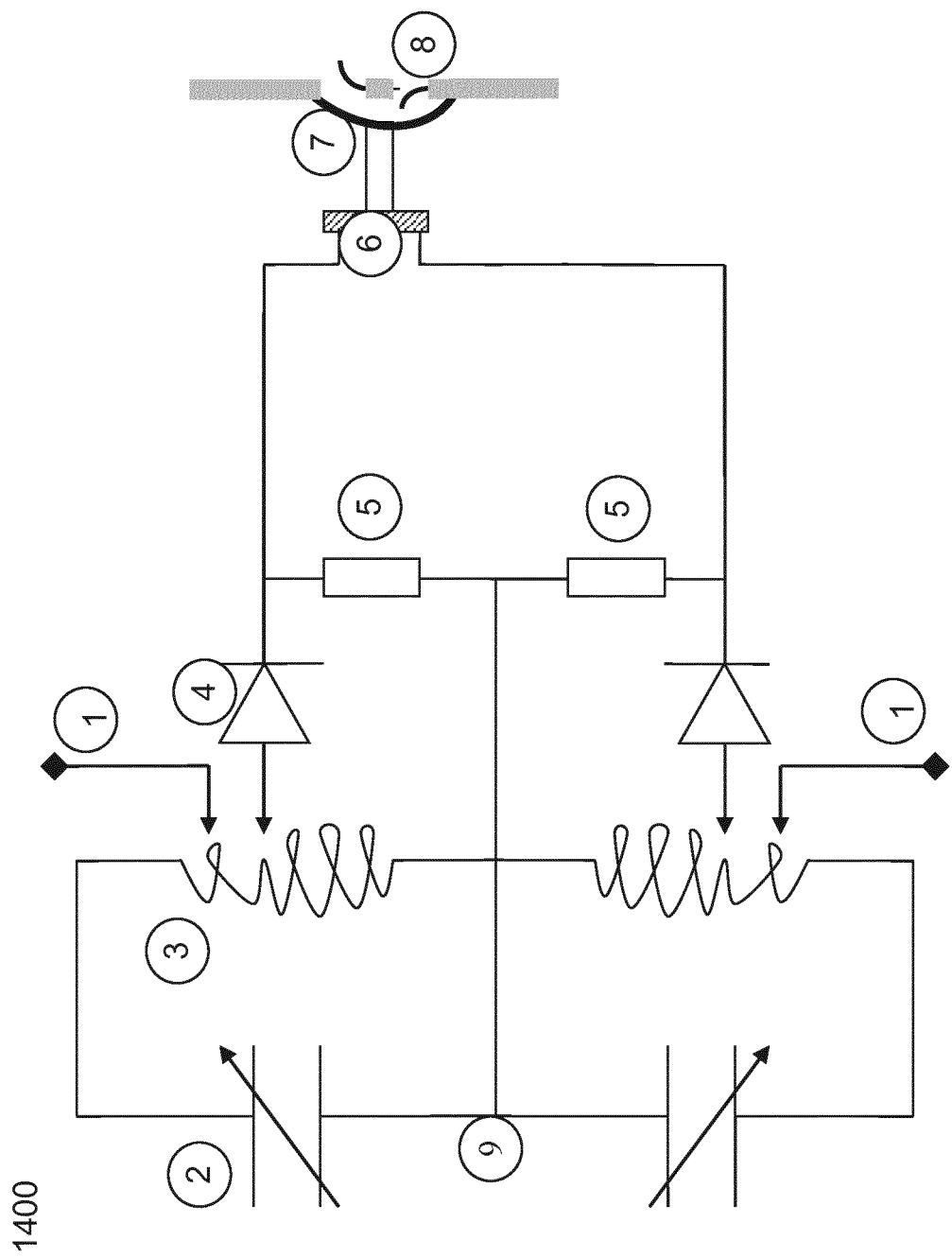
FIG. 13 is a circuit diagram of an energy harvester according to another embodiment.

In some embodiments, the circuit can have multiple (e.g., back to back) antenna arrays. For example, FIG. 13 illustrates a circuit 1400 having paired antennas 1, which may be straight or coils. The paired antennas 1 are arranged around (e.g., symmetrical to) a virtual earth (or ground) 9 at the center of the circuit 1400. The two halves of the system can act as a mirror image allowing the system to work without an earth (or ground). If the antennas 1 are coils, they may be connected together. If the antennas are not connected to each other they should be in physical opposition. Alternating current harvested by the circuit 1400 appears across the resistors 5.

In some embodiments, one or more aerials, transducers, and/or antennas can be positioned on and/or incorporated into a dressing and/or built within the dressing. Alternatively or additionally, in some embodiments, one or more aerials, transducers, and/or antennas can be positioned on and/or incorporated into the surface of a negative pressure wound therapy device (such as a negative pressure wound therapy pump). In some embodiments, the drive signal that can be used to generate negative pressure wound therapy can utilize multiple aerials, inductive, and capacitive elements that can be used to generate a standing electrical wave between the aerials to directly trigger piezoelectric and/or other electroactive materials in order to cause a mechanical pumping action.

In certain embodiments, the one or more aerials, transducers, and/or antennas can be woven into, layered within, and/or positioned on the surface of the dressing or device. The one or more aerials, transducers, and/or antennas can be incorporated into the device and/or dressing with associated inductive and capacitive elements to tune the circuit to one or more frequencies. Additionally, in some embodiments, a transformer can be utilized to increase the potential of the harvested power signal. The one or more aerials, transducers, and/or antennas may be paired in phase and/or antiphase pairs to emulate an earth potential. In some embodiments, the signal generated can be used to generate negative pressure wound therapy. In some embodiments, the pump used for the negative pressure wound therapy can be any pump as described herein or any other suitable pump. The pump can utilize a voice coil transducer, the pump can be a peristaltic pump and/or piezoelectric pump. In some embodiments, the harvested power signal can be used to power other components of the dressing and/or negative pressure therapy system device other than the pump including, but not limited to, sensor components (which can be positioned proximate or within the wound), a controller or control unit, and/or a computer.

In some embodiments, the RF power picked up or harnessed by the harvesting device can be used to operate other elements in the dressing. For example, the power can be used to operate sensing elements in the dressing. In some embodiments, the harvester can power remote sensors. In some embodiments, remote sensors powered by the harvester can include pressure, temperature, pH, humidity sensors, and/or other sensors incorporated into the negative pressure therapy system. In some embodiments, the remote sensors can communicate wirelessly with the controller. In some embodiments, the remote sensors can communicate wirelessly with a remote computer. In some embodiments, the controller can communicate wirelessly with a remote computer. In some embodiments, the remote sensors, controller, remote computer, and/or other components of the negative pressure therapy system can communicate through electrical wiring incorporated into the dressing, tubing, pump, and/or other components of the negative pressure therapy device. In some embodiments, the power harnessed by the harvesting device can be used to operate communications elements in the dressing.

In some embodiments, the level of energy harvested or generated to keep the negative pressure therapy system running can be low, such as on the order of a few mW. The negative pressure wound therapy system can have a continuous average maximum draw of about 40 mW over a 24-hour period. The power transmitted by a charging device can depend on the efficiency of the coupling. In some embodiments, the charging device can transmit between about 100 mW to about 120 mW over an 8 hours period and about 1 W to about 3 W over a 1 to 3 hour period. In some embodiments, the device can transmit about 1 W to about 3 W over a period of more than 3 hours. This can account for efficiency losses during broadcast and reception.

In some embodiments, the negative pressure wound therapy system can use transmitted power as an AC signal. For example, all unwanted frequencies can be shorted to ground. AC signal power can range from 100-200 mW. In some embodiments, a DC signal can be used after being rectified by a suitable rectifier. In some embodiments, when power is transmitted at lower frequencies, using a DC signal for powering the negative pressure wound therapy system could be more efficient than using an AC signal. In some embodiments, such as when power is transmitted at frequency or frequencies ranging in GHz (for example, when cell phone spectrum is used), using AC signal for powering the negative pressure wound therapy system can be more efficient.

In some embodiments, a transducer can be used to generate an electrical signal at a frequency of 1/x of the aerial tuned frequency, where x is divisible by 0.5 (e.g. 0.5, 1, 1.5, 2, 2.5 etc.) to within a 10% error (e.g., x=0.45-0.55, 0.95-1.05 etc.). This may be achieved is by having a fixed-frequency oscillator that is driven by impulses from the driving circuit.

In some embodiments, the harvester can generate direct current by using a suitable rectifier. Generated direct current can then be used by the operational elements of the system, such as pump(s), CPU(s) or controller(s), sensor(s), and other elements. Alternatively or additionally, direct current can be used to charge an energy storage device, such as one or more capacitors. In some embodiments, the energy storage device can be used as a direct energy charger or charging station. In some embodiments, the harvesting device can charge rechargeable batteries. The power transmitted could be related to the rate of charging the battery.

In some embodiments, the harvesting device can include one or more sensing elements that can identify the frequencies available to harness the energy from. For example, when the harvesting device senses multiple frequencies from which to obtain power, the harvesting device can scan the best places to harvest the energy from. In some embodiments, the one or more sensing elements can be used to identify the frequency or frequencies from which the highest power may be harvested. In some embodiments, a single frequency that exists everywhere can be used to give enough power to scan for another frequency or frequencies to harvest power.

In some embodiments, the device may also have one or more computational elements (such as one or more controllers) to identify the most powerful frequency spectrum boundaries to harvest the highest power from the available ambient RF signals. In some embodiments, the harvester can initially harvest from a fixed frequency to generate the power to drive the one or more computational elements. The one or more computational elements can then identify another frequency spectrum and tune a secondary aerial or array to harvest energy from that spectrum to maximize the available charge for primary device function.

In some embodiments, the aerial(s) can be tuned to one or more of the following frequencies: about 698-894 MHz, about 1.392-1.395 GHz, about 1.432-1.435 GHz, about 1.710-1.755 GHz, about 1.850-1.910 GHz, about 1.930-1.990 GHz, about 2.110-about 2.155 GHz, about 2.4-2.496 GHz, about 2.496 GHz-2.690 GHz, about 3.657-3.693 GHz, about 4.915-5.825 GHz, and about 5.850-5.925 GHz. These frequency spectrums can correspond to heavily populated spectrums, such as WiFi and cell phone ranges (2G, 3G, 4G) for various countries around the world. That is, in some embodiments, the device can utilize wasted carrier signal and not actual broadcast data for charging.

In some embodiments, the aerial(s) can be tuned to about 58-62 GHz and a portion of the energy can be used to send a signal back to the source to identify beam propagation pathways. This suggested range can be for ultra-high speed Wi-Fi (high GHz signal which is very dense and may not go around obstacle due to having a very small wavelength (e.g., c/60 GHz=~5 millimeters)). Methods for determining beam propagation pathway(s) can be used to lock in on the transmission source. For example, antenna(s) can be moved, such as rotated. In some embodiments, small antennas (e.g., millimeter or sub-millimeter scale antenna) can be printed on a printed circuit board or another substrate. In some embodiments, half-wavelength or quarter-wavelength resonator antennas can be used to pick up the transmission.

In some embodiments, a harvesting device can utilize a supercapacitor, battery, and/or other intermediate charge sink to store charge from the harvesting device to allow greater power output at a lower duty cycle. In some embodiments, a specific signal can be generated by a charging device or station for the express purpose of running or recharging the dressing. In some embodiments, the device can include a thermal energy harvester system or light reactive system to bolster the generating capacity of the system. In some embodiments, the light reactive system can be UV, visible, or IR frequency range.

In various embodiments, an indicator and/or an alarm can be used to identify that the system is close to its low energy operation threshold and/or where the system includes a charge store as described herein and when that stored charge is low. In some embodiments, the packaging of the dressing can be designed to specifically shield the device placed in the dressing from one or more operational frequencies. For example, a metal or metallically coated RF-shielding package can be used to shield the device from elements in the atmosphere. Once the device is removed from the packaging, the device can be initiated. That is, exposing the device to RF waves can indicate or cause activation, which may start a timer, such as operational timer. In some embodiments, the timer system can be used as a sterility check. For example, when the device is exposed to RF waves, a timer counts the time beyond a threshold that indicates sterility is lost. In the alternative, a chemical means can be used to determine exposure to the atmosphere to check whether sterility is lost.

In some embodiments, opening the packaging initiates or activates the system. This can be performed with or without a delay. In some embodiments, the exposure of the device to RF after opening initiates an operational timer. The operational timer can identify whether the device has been used within a specific time. The operational timer can also operate one or more indicators that identify that the device should not be used due to over use, risk of contamination, and/or loss of sterility. In some embodiments, the operational timer can identify whether the device has not been used within a specific time by, without limitation, inductive sensing of contact with the skin, successful generation of negative gauge pressure, and the like. In some embodiments, the operational timer can be used to identify or determine end of life of the device. For example, device can be deactivated when the operational timer reaches 1 day, 3 days, 4 days, 10 days, 30 days or any other suitable duration.

In some embodiments, a charging station can use feedback from the device to direct the energy output towards the device. The feedback from the device can be line of sight or rebounding from objects. For example, initially the charging station can either send omnidirectionally or sweep directions to identify the best path to the negative pressure wound therapy system. The charging station can then direct its output in the identified direction. In some embodiments, this can be accomplished by directing the energy to arrays which point in the desired direction and/or by moving the transmitting antenna. In some embodiments, the charging station can track the movement of the receiver. In some embodiments, the charging station can have an identification system that the receiver is in range before significant amount of power is transmitted. In some embodiments, the lower-level power mode with minimum power requirement can be used (e.g., similar to that of Bluetooth 4.0) until the receiver is in range. Once the receiver is in range, higher power level can be transmitted.

Harvesting devices described herein operate differently than crystal radios in ways that are beneficial for the use of harvesting devices as a power source for wound dressings and negative pressure systems. For example, crystal radios utilizes RF harvesting to generate a noise signal. One of the problems with crystal radios is the low selectivity and poor sound quality. In some embodiments, to harvest the greatest amount of power from the ambient RF environment a wider frequency band could be used for the harvesting device. Crystal radios operate only on AM bandwidths when trying to reproduce signals. However, in some embodiments, for the harvesting device, the carrier frequency can be the primary harvesting mode. In such embodiments, FM (and/or higher frequency) signals can be used to generate the operating function, particularly where a rectifying antenna is used as described herein. Discloses embodiments of RF harvesting can be combined with low power pumps and/or sensing systems.

Other Embodiments

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. Accordingly, the scope of the present disclosure is defined only by reference to the appended claims.

Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An apparatus for use in negative pressure wound therapy, comprising:
 a source of negative pressure;
 a port configured to be in fluid communication with a dressing configured to be placed over a wound; and
 one or more indicators configured to illuminate and communicate information; and
 a controller configured to operate the one or more indicators in:
  an operational status mode at a first frequency selected to communicate first status information to a user; and
  a data transmission mode at a second frequency selected to communicate second status information encoded in an illumination pattern of the one or more indicators to an electronic device comprising at least one camera configured to capture the illumination pattern of the one or more indicators transmitted at the second frequency and decode the illumination pattern to determine the second status information.

2. The apparatus of claim 1, wherein the one or more indicators comprise different color LEDs.

3. The apparatus of claim 2, wherein the one or more indicators are configured to flash between the different colors.

4. The apparatus of claim 3, wherein the different colors comprise red and green.

5. The apparatus of claim 1, wherein the electronic device comprises a smartphone or a tablet.

6. The apparatus of claim 1, wherein the one or more indicators comprise four indicators.

7. The apparatus of claim 6, wherein the one or more indicators transmit four bits of data at a time to the electronic device.

8. The apparatus of claim 1, wherein the illumination pattern of the one or more indicators is configured to communicate the second status information at a rate of approximately 40 bit/second to approximately 1 Kbit/second.

9. A method of operating an apparatus for use in negative pressure wound therapy, comprising:
 by a controller of the apparatus, operating one or more indicators of the apparatus, the one or more indicators communicating status of at least one of a pump assembly of the apparatus configured to be fludicially connected to a dressing positioned over a wound or the dressing through an illumination pattern of the one or more indicators positioned on an exterior surface of the pump assembly, the controller operating the one or more indicators in:
  an operational status mode at a first frequency selected to communicate first status information to a user; and
  a data transmission mode at a second frequency selected to communicate second status information encoded in an illumination pattern of the one or more indicators to an electronic device comprising at least one camera, thereby enabling the electronic device having at least one camera to capture the illumination pattern of the one or more indicators transmitted at the second frequency and decode the illumination pattern to determine the second status information.

* * * * *

UNITED STATES PATENT AND TRADEMARK OFFICE
CERTIFICATE OF CORRECTION

PATENT NO. : 10,828,403 B2
APPLICATION NO. : 15/540229
DATED : November 10, 2020
INVENTOR(S) : Ben Alan Askem et al.

Page 1 of 1

It is certified that error appears in the above-identified patent and that said Letters Patent is hereby corrected as shown below:

On the Title Page

In Column 2, item (56), Other Publications, Lines 1-2, delete "Appication" and insert --Application--.

In the Specification

In Column 2, Line 52, delete "fludicially" and insert --fluidically--.

In Column 3, Lines 23-24, delete "fludicially" and insert --fluidically--.

In Column 12, Line 7, delete "can by" and insert --can be--.

In the Claims

In Column 26, Line 24, Claim 9, delete "fludicially" and insert --fluidically--.

Signed and Sealed this
Nineteenth Day of January, 2021

Andrei Iancu
*Director of the United States Patent and Trademark Office*